United States Patent
Bachelder et al.

(10) Patent No.: US 10,433,756 B1
(45) Date of Patent: Oct. 8, 2019

(54) ADJUSTABLE GEOMETRY WEARABLE ELECTRODES

(71) Applicant: CeriBell, Inc., Mountain View, CA (US)

(72) Inventors: Brad G. Bachelder, Menlo Park, CA (US); Xingjuan Chao, Palo Alto, CA (US)

(73) Assignee: CeriBell, Inc., Mountain View, CA (US)

(*) Notice: Subject to any disclaimer, the term of this patent is extended or adjusted under 35 U.S.C. 154(b) by 0 days.

(21) Appl. No.: 16/017,568

(22) Filed: Jun. 25, 2018

Related U.S. Application Data

(60) Provisional application No. 62/678,416, filed on May 31, 2018.

(51) Int. Cl.
*A61B 5/0478* (2006.01)
*A61B 5/00* (2006.01)
(Continued)

(52) U.S. Cl.
CPC ........ *A61B 5/0478* (2013.01); *A61B 5/04025* (2013.01); *A61B 5/04026* (2013.01);
(Continued)

(58) Field of Classification Search
CPC ... A61B 5/0404; A61B 5/0408; A61B 5/0416; A61B 5/0478; A61B 5/0492
See application file for complete search history.

(56) References Cited

U.S. PATENT DOCUMENTS 3,474,775 A    10/1969   Johnson
3,580,240 A *   5/1971   Cosentino ............ A61B 5/0408
                                                                        600/392

(Continued)

FOREIGN PATENT DOCUMENTS

DE            2644236       *   4/1978
DE            2644236 A1     4/1978
WO    WO-2017172742 A1    10/2017

OTHER PUBLICATIONS

International search report with written opinion dated Jul. 31, 2017 for PCT/US2017/024505.

(Continued)

*Primary Examiner* — Lee S Cohen
(74) *Attorney, Agent, or Firm* — Wilson Sonsini Goodrich and Rosati, P.C.

(57) ABSTRACT

The present disclosure provides systems, apparatuses, and methods for use of wearable electrode assemblies. The electrode assemblies improve comfort by providing increased overall surface area of their bottom surfaces, which make contact with the patient's scalp and hair. Collapse, compression, or telescoping of the bottom surface will thereby decrease the direct force and/or pressure applied by the distal member or members of the bottom surfaces to the skin. This may be advantageous in patients who have little to no hair in electrode contact areas, patient populations that are particularly skin-sensitive, and/or patients which must wear the electrode assemblies of an extended time period. The electrode assemblies further include structures to dispense and/or maintain conductive gel placed over the patient's skin, thereby maintaining electrical connection quality, and/or to facilitate the clearing of skin and/or hair prior to establishing an electrical connection.

29 Claims, 20 Drawing Sheets

(51) Int. Cl.
  *A61B 5/0402* (2006.01)
  *A61B 5/0408* (2006.01)
  *A61B 5/0492* (2006.01)

(52) U.S. Cl.
  CPC ........ *A61B 5/04085* (2013.01); *A61B 5/0492* (2013.01); *A61B 5/6803* (2013.01); *A61B 5/6843* (2013.01); *A61B 5/6844* (2013.01); *A61B 2562/0217* (2017.08); *A61B 2562/043* (2013.01); *A61B 2562/14* (2013.01)

(56) References Cited

U.S. PATENT DOCUMENTS

| | | | |
|---|---|---|---|
| 3,602,216 A | | 8/1971 | Moe, Jr. |
| 3,776,228 A | | 12/1973 | Semler |
| 3,830,229 A | | 8/1974 | Johnson |
| 4,033,334 A | | 7/1977 | Fletcher |
| 4,079,731 A | | 3/1978 | Danby |
| 4,137,909 A | * | 2/1979 | Hix ............ A61B 5/0408 600/392 |
| 4,166,457 A | | 9/1979 | Jacobsen et al. |
| 4,215,696 A | * | 8/1980 | Bremer ............ A61B 5/0408 600/392 |
| 4,458,687 A | | 7/1984 | Dickson |
| 4,693,711 A | * | 9/1987 | Bremer ............ A61B 5/0408 604/306 |
| 4,709,702 A | | 12/1987 | Sherwin |
| 4,919,148 A | | 4/1990 | Muccio |
| 5,037,380 A | * | 8/1991 | Jacobsen ............ A61N 1/0448 604/20 |
| 5,273,037 A | | 12/1993 | Itil et al. |
| 5,309,909 A | * | 5/1994 | Gadsby ............ A61B 5/0408 600/386 |
| 5,357,957 A | | 10/1994 | Itil et al. |
| 5,404,875 A | * | 4/1995 | Gevins ............ A61B 5/0478 600/372 |
| 5,628,729 A | * | 5/1997 | Okabe ............ A61N 1/0436 604/20 |
| 6,366,795 B1 | * | 4/2002 | Bremer ............ A61B 5/0408 600/395 |
| 6,381,481 B1 | | 4/2002 | Levendowski et al. |
| 6,640,118 B2 | * | 10/2003 | Van Heerden ....... A61N 1/0492 600/372 |
| 6,640,122 B2 | | 10/2003 | Manoli et al. |
| 6,952,605 B1 | | 10/2005 | Scarberry |
| 7,424,319 B2 | * | 9/2008 | Muehlsteff ............ A61N 1/0492 600/372 |
| 7,841,301 B2 | | 11/2010 | Mainini et al. |
| 8,805,470 B2 | | 8/2014 | Afanasewicz et al. |
| 9,408,575 B2 | | 8/2016 | Bordoley et al. |
| 9,820,670 B2 | | 11/2017 | Parvizi et al. |
| 2007/0255127 A1 | | 11/2007 | Mintz et al. |
| 2007/0272313 A1 | | 11/2007 | Olds |
| 2015/0112153 A1 | | 4/2015 | Nahum |
| 2015/0313498 A1 | | 11/2015 | Coleman et al. |
| 2016/0022165 A1 | | 1/2016 | Sackellares et al. |
| 2016/0022981 A1 | | 1/2016 | Wingeier et al. |
| 2017/0165485 A1 | | 6/2017 | Sullivan et al. |
| 2017/0281036 A1 | | 10/2017 | Parvizi et al. |
| 2018/0049661 A1 | | 2/2018 | Parvizi et al. |

OTHER PUBLICATIONS

Notice of allowance dated Jul. 24, 2017 for U.S. Appl. No. 15/387,381.
Office action dated Apr. 18, 2017 for U.S. Appl. No. 15/387,381.
International Search Report and Written Opinion for PCT/US2019/034149 dated Aug. 1, 2019.

\* cited by examiner

ADJUSTABLE GEOMETRY WEARABLE ELECTRODES

CROSS-REFERENCE

This application claims the benefit of U.S. Provisional Application No. 62/678,416, filed May 31, 2018, the entirety of which are incorporated herein by reference.

The subject matter of this application is related to the subject matter of U.S. patent application Ser. No. 15/387,381 filed Oct. 13, 2017, now issued on Nov. 21, 2017 as U.S. Pat. No. 9,820,670, U.S. patent application Ser. No. 15/783,346 filed Oct. 13, 2017, and PCT Application No. PCT/US2017/024505 filed on Mar. 28, 2017, the contents of which are fully incorporated herein by reference.

BACKGROUND

The present disclosure relates to methods and apparatuses for placing one or more electrodes against the skin surface of a patient and monitoring a patient status. More particularly, the present disclosure relates to methods and apparatuses for facilitating the speed and efficiency for placing one or more electrodes against a patient's scalp, optionally in combination with tracking the movements of a patient. The present disclosure further relates to methods and apparatuses for comfortable and extended wear of one or more electrodes against a patient's scalp for a variety of patient settings.

Uniform contact between the metal electrode and the skin may be beneficial for electrodes used in electrocardiography and electroencephalography to prevent electrical noise due to the interface between the electrode and skin surface. To provide for uniform contact with the skin area, a conductive gel may be applied to the skin surface to facilitate electrical conduction with the electrode. However, when electrodes are placed at multiple locations over the patient's scalp, the application of the gel in combination with determining electrode placement may require specialized training and skill but may also be very time consuming.

Some electrodes utilize conductive gel interfaces which are pre-formed for contacting the electrode; however, the gel interfaces may become ineffective when hair is present and may sometimes require the removal of the underlying hair.

Specialized electrode assemblies which dispense gel as they are worn and contacted against a patient's scalp have been developed. These electrode assemblies, however, may be uncomfortable for extended wear, such as when the patient is resting upon a pillow or other platform during sleep. Further, gel loss may occur over time with these electrode assemblies and connection quality may dip during extended wear.

Accordingly, there exists a need for methods and devices which facilitate the speed of placing electrodes. There also exists a need for facilitating contact between the electrode and the skin surface even in the presence of hair. It may be preferable to provide methods and devices which simplify or reduce the necessity of preparing the hair and scalp for each electrode contact. It may be desirable if such methods and devices could provide for incorporation of a conductive fluid or gel as part of the electrode assembly as well as for preserving such conductive fluids or gels for extended time periods. It may be desirable if such methods and devices facilitate comfortable extended wear for the patient.

SUMMARY

The present disclosure provides systems, apparatuses, and methods for use of electrode assemblies, which may be wearable by a user or patient. Electrode assemblies provided herein may improve comfort by increasing the overall surface area of the electrode assembly bottom surface, which may make contact with the patient's skin (e.g., scalp) and hair. Collapse, compression, or telescoping of the bottom surface may thereby decrease the direct force and/or pressure applied by the distal member(s) of the electrode assembly bottom surface to the skin. This may be advantageous in patients who have little to no hair in electrode contact areas, patients that are particularly skin-sensitive, and/or patients which must wear the electrode assemblies for an extended time period. The electrode assemblies may include structures to dispense and/or maintain conductive gel placed over the patient's skin, thereby maintaining electrical connection quality. The electrode assemblies described herein may also facilitate the clearing of skin and/or hair prior to establishing an electrical connection with the skin.

Aspects of the present disclosure provide electrode assemblies. An exemplary electrode assembly may comprise an electrode body defining an interior reservoir for storing a tissue conductive fluid or gel and having a bottom opening to dispense the tissue conductive fluid or gel. The electrode body may be at least partially adjustable, collapsible, or compressible in a direction toward the skin.

The electrode body may be at least partially collapsible or compressible in response to an increase in force applied on the electrode body in the direction toward the skin.

The electrode body may comprise a first body member and a second body member operatively coupled to one another. One or more of the first body member or the second body members may be conductive. The first body member and the second body members may be coaxial. The first and second body members may be configured to telescope relative to one another in response to the increase in force. For example, the second body member may be spring-loaded within the first body member. The first body member may be rigid and the second body member may be flexible and resiliently collapsible in response to the increase in force. The second body member may be elastomeric. The first body member may have a cylindrical shape and the second body member may have a conical shape. The bottom opening may be provided on the second body member. The electrode body may have a central axis and the bottom opening may be off-set from the central axis.

The electrode body may be at least partially depressible to dispense the tissue conductive fluid or gel through the bottom opening. The electrode body may comprise a depressible top surface or button. The electrode body may comprise a depressible lateral surface or button.

The electrode body may comprise an adaptor for an external dispenser of the tissue conductive fluid or gel. The electrode body may have an upper surface and the adapter may be positioned at the upper surface. The external dispenser may comprise one or more of a syringe, a manual squeeze tube, or a roller squeeze tube. The adaptor may be configured to removably couple to the external dispenser such that the external dispenser is movable relative to the electrode body. The external dispenser may comprise a skin preparing surface. Movement of the external dispenser relative to the electrode body may clear one or more of skin or hair of the subject when the external dispenser is removably coupled to the adaptor and moved. The skin preparing surface may be one or more of rigid or abrasive. The external dispenser may be movable relative to the electrode body by one or more of translation, rotation, or pivoting. The electrode body may comprise one or more stencil elements having one or more slots through which the skin preparing surface of the external dispenser to guide movement of the external dispenser relative to the electrode body. The adaptor may further comprise a valve to prevent backflow of the tissue conductive fluid or gel.

The electrode body may comprise a skin preparing surface adjacent the bottom opening. The electrode body may be movable relative to a body of the wearable sensor apparatus to clear one or more of skin or hair of the subject. The skin preparing surface adjacent of the electrode body may be one or more of rigid or abrasive. The electrode body may be movable relative to the body of the wearable sensor by one or more of translation, rotation, or pivoting.

The electrode assembly may further comprise a protective skirt configured to couple to the electrode body. The protective skirt may have an increased surface area base to minimize exposure of skin adjacent the distal opening of the electrode body to an external environment. The protective skirt may be configured to removably couple to the electrode body. The protective skirt may be spring-loaded onto the electrode body. The protective skirt may be resiliently compressible relative to the electrode body. The protective skirt and the electrode body may be coaxial when coupled to one another.

The electrode body may comprise a bottom surface. The bottom surface may have one or more containment features for containing the tissue conductive gel or fluid that has been dispensed through the bottom opening. The one or more containment features may comprise a plurality of protrusions or fingers.

Aspects of the present disclosure provide methods of continuously monitoring a subject. In an exemplary method, a wearable sensor apparatus may be provided to be placed over skin of the subject such that at least one electrode assembly of the wearable sensor apparatus is adjacent the skin. Movement of the at least one electrode assembly relative to a body of the wearable sensor apparatus may be accommodated to clear one or more of skin particles or hair from the skin. Tissue conductive fluid or gel may be dispensed from the at least one electrode assembly in response to a compressive force. An electrode body of the at least one electrode assembly may be at least partially adjusted, collapsed, or compressed in a direction toward the skin.

The at least one electrode assembly may be at least partially collapsed or compressed in response to an increase in force applied on the electrode body in the direction toward the skin. The movement of the at least one electrode assembly relative to the body of the wearable sensor apparatus may comprise one or more of translation, rotation, or pivoting. The movement of the at least one electrode assembly relative to the body of the wearable sensor apparatus may move a skin preparing surface of the electrode body to clear the one or more of skin particles or hair from the skin.

The conductive fluid or gel may be dispensed in response to the compressive force applied to a top surface or button of the electrode body of the at least one electrode assembly. The conductive fluid or gel may be dispensed in response to the compressive force applied to a lateral surface or button of the electrode body of the at least one electrode assembly. The tissue conductive fluid or gel may be dispensed by coupling an external dispenser to the electrode body of the at least one electrode assembly and actuating the external dispenser.

To at least partially collapse or compress the electrode body, a second body member of the electrode body may be telescoped relative to a first body member of the electrode body. Alternatively or in combination, to at least partially collapse or compress the electrode body, a flexible body member of the electrode body may be compressed or collapsed. The flexible body member may be elastomeric.

The electrode body of the at least one electrode assembly may be coupled with a protective skirt. The protective skirt may have an increased surface area base to minimize exposure of skin adjacent a distal opening of the electrode body to an external environment.

The skin of the subject may comprise a scalp.

The wearable sensor apparatus may comprise one or more of an EEG sensor, an EKG sensor, or an EMG sensor.

The wearable sensor apparatus may comprise a wearable headband. The increase in force applied on the electrode body in the direction toward the skin may be from resting a head of the subject against a surface. The surface may comprise one or more of a pillow, a bed, a headrest, or a platform.

Aspects of the present disclosure may provide electrode assemblies. An exemplary electrode assembly may comprise an electrode body defining an interior reservoir for storing a tissue conductive fluid or gel and having a bottom opening to dispense the tissue conductive fluid or gel. The electrode body may comprise an adaptor for an external dispenser of the tissue conductive fluid or gel. The interior reservoir of the electrode body may receive the tissue conductive fluid or gel dispensed by the external dispenser before dispensing through the bottom opening of the electrode body.

The external dispenser may comprise one or more of a syringe, a manual squeeze tube, or a roller squeeze tube.

The adaptor may be configured to removably couple to the external dispenser such that the external dispenser is movable relative to the electrode body. The external dispenser may comprise a skin preparing surface. Movement of the external dispenser relative to the electrode body may clear one or more of skin or hair of the subject when the external dispenser is removably coupled to the adaptor and moved. The skin preparing surface may be one or more of rigid or abrasive. The external dispenser may be movable relative to the electrode body by one or more of translation, rotation, or pivoting. The electrode body may comprise one or more stencil elements having one or more slots through which the skin preparing surface of the external dispenser to guide movement of the external dispenser relative to the electrode body.

The adaptor may further comprise a valve to prevent backflow of the tissue conductive fluid or gel.

At least a portion of the electrode body may be collapsible or compressible. At least a portion of the electrode body may be resiliently collapsible or compressible. Alternatively or in combination, at least a portion of the electrode body may be telescoping. At least a portion of the electrode body may be collapsible or compressible in response to an increase in force applied on the electrode body in a direction toward the skin.

The electrode assembly may further comprise a protective skirt configured to couple to the electrode body. The protective skirt may have an increased surface area base to minimize exposure of skin adjacent the distal opening of the electrode body to an external environment. The protective skirt may be configured to removably couple to the electrode body. The protective skirt may be spring-loaded onto the electrode body. The protective skirt may be resiliently compressible relative to the electrode body. The protective skirt and the electrode body may be coaxial when coupled to one another.

The electrode body may comprise a bottom surface. The bottom surface may have one or more containment features for containing the tissue conductive gel or fluid that has been dispensed through the bottom opening. The one or more containment features may comprise a plurality of protrusions or fingers.

Aspects of the present disclosure may further provide electrode assembly systems comprising any of the electrode assemblies disclosed herein and any of the external dispensers disclosed herein.

Aspects of the present disclosure may provide methods of continuously monitoring a subject. A wearable sensor apparatus may be provided to be placed over skin of the subject such that at least one electrode assembly of the wearable sensor apparatus is adjacent the skin. An external dispenser may be coupled to an electrode body of the at least one electrode assembly. The external dispenser may be actuated to dispense tissue conductive fluid or gel from external dispenser into an interior reservoir of the electrode body.

Movement of the at least one electrode assembly relative to a body of the wearable sensor apparatus may be accommodated to clear one or more of skin particles or hair from the skin. Movement of the at least one electrode assembly relative to the body of the wearable sensor apparatus may comprise one or more of translation, rotation, or pivoting.

Movement of the external dispenser relative to the at least one electrode assembly coupled thereto may be accommodated to clear one or more of skin particles or hair from the skin. The movement of the at least one electrode assembly relative to the body of the wearable sensor apparatus may comprise one or more of translation, rotation, or pivoting.

The movement of the at least one electrode assembly relative to the body of the wearable sensor apparatus may move a skin preparing surface of the electrode body to clear the one or more of skin particles or hair from the skin.

The external dispenser may be coupled to the electrode body by removably coupling the external dispenser to an adaptor of the electrode body. The adaptor may be positioned on an upper surface of the electrode body. The adaptor may be positioned on a lateral surface of the electrode body. The adaptor may further comprise a valve to prevent backflow of the tissue conductive fluid or gel.

The external dispenser may comprise one or more of a syringe, a manual squeeze tube, or a roller squeeze tube.

The electrode body of the at least one electrode assembly may be coupled with a protective skirt. The protective skirt may have an increased surface area base to minimize exposure of skin adjacent a distal opening of the electrode body to an external environment.

The skin of the subject may comprise a scalp.

The wearable sensor apparatus may comprise one or more of an EEG sensor, an EKG sensor, or an EMG sensor.

The wearable sensor apparatus may comprise a wearable headband. The increase in force applied on the electrode body in the direction toward the skin may be from resting a head of the subject against a surface. The surface may comprise one or more of a pillow, a bed, a headrest, or a platform.

Aspects of the present disclosure provide electrode assemblies for use with wearable sensor apparatus(es) to be placed over skin of a subject. An exemplary electrode assembly may comprise an electrode body and a protective skirt. The electrode body may define an interior reservoir for storing a tissue conductive fluid or gel and having a bottom opening to dispense the tissue conductive fluid or gel. The protective skirt may be configured to couple to the electrode body. The protective skirt may have an increased surface area base to minimize exposure of skin adjacent the distal opening of the electrode body to an external environment.

The protective skirt may be configured to removably couple to the electrode body.

The protective skirt may be spring-loaded onto the electrode body.

The protective skirt may be resiliently compressible relative to the electrode body.

The protective skirt and the electrode body may be coaxial when coupled to one another.

The electrode body may comprise an adaptor for an external dispenser of the tissue conductive fluid or gel. The interior reservoir of the electrode body may receive the tissue conductive fluid or gel dispensed by the external dispenser before dispensing through the bottom opening of the electrode body. The external dispenser may comprise one or more of a syringe, a manual squeeze tube, or a roller squeeze tube. The adaptor may be configured to removably couple to the external dispenser such that the external dispenser is movable relative to the electrode body. The external dispenser may comprise a skin preparing surface. Movement of the external dispenser relative to the electrode body may clear one or more of skin or hair of the subject when the external dispenser is removably coupled to the adaptor and moved. The skin preparing surface may be one or more of rigid or abrasive. The external dispenser may be movable relative to the electrode body by one or more of translation, rotation, or pivoting. The electrode body may comprise one or more stencil elements having one or more slots through which the skin preparing surface of the external dispenser to guide movement of the external dispenser relative to the electrode body. The adaptor may further comprise a valve to prevent backflow of the tissue conductive fluid or gel.

At least a portion of the electrode body may be collapsible or compressible, such as resiliently collapsible or compressible. Alternatively or in combination, at least a portion of the electrode body may be telescoping. The portion of the electrode body may be collapsible or compressible in response to an increase in force applied on the electrode body in a direction toward the skin.

The electrode body may comprise a bottom surface. The bottom surface may have one or more containment features for containing the tissue conductive gel or fluid that has been dispensed through the bottom opening. The one or more containment features may comprise a plurality of protrusions or fingers.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present disclosure are set forth with particularity in the appended claims. A better understanding of the features and advantages of the present disclosure will be obtained by reference to the following detailed description that sets forth illustrative embodiments, in which the principles of the invention are utilized, and the accompanying drawings of which:

DETAILED DESCRIPTION

The present disclosure relates to systems, systems, apparatuses, and methods for use of an electrode assembly, which may be wearable by a user. Electrode assemblies of the present disclosure may improve comfort by increasing the overall surface area of the electrode assembly bottom surface which may make contact with the patient's scalp and hair. For instance, as force and/or pressure is applied from the electrode assembly to the skin, the electrode assembly may be configured to increase the surface area of contact. Collapse, compression, or telescoping of the bottom surface may thereby decrease the direct force applied by the distal member or members of the electrode assembly bottom surface. This may be advantageous in patients who have little to no hair in electrode contact areas, patients that are particularly skin-sensitive, and/or patients which must wear the electrode assemblies for an extended time period.

Embodiments of the present disclosure include apparatuses with structures to dispense a conductive fluid or gel to improve contact between an electrode assembly and a patient skin. Embodiments of the present may improve upon existing electrode assemblies by providing a valve which allows for repeated filling of the electrode with conductive gel to counteract gel evaporation or drying. These embodiments may be beneficial for extended wear and continuous signal collection and electrode use.

Embodiments of the present disclosure may facilitate the speed of placing electrodes by integration of the electrodes into a wearable electrode assembly. Additionally or alternatively, embodiments of the present disclosure may facilitate refilling of the conductive liquid or gel in order to improve electrical contact over longer measurement periods, such as when the gel may have dried. Optionally, in any embodiment, electrode assemblies disclosed herein may be combined with systems for tracking the movement of a patient, such as with accelerometers and/or optical tracking.

Embodiments of the present disclosure may comprise embodiments, variations, and examples of the electrode carrier assemblies of commonly assigned U.S. patent application Ser. No. 15/387,381 filed Oct. 13, 2017, now issued on Nov. 21, 2017 as U.S. Pat. No. 9,820,670, U.S. patent application Ser. No. 15/783,346 filed Oct. 13, 2017, and PCT Application No. PCT/US2017/024505 filed on Mar. 28, 2017, which are incorporated herein by reference in their entirety.

Figure 1:
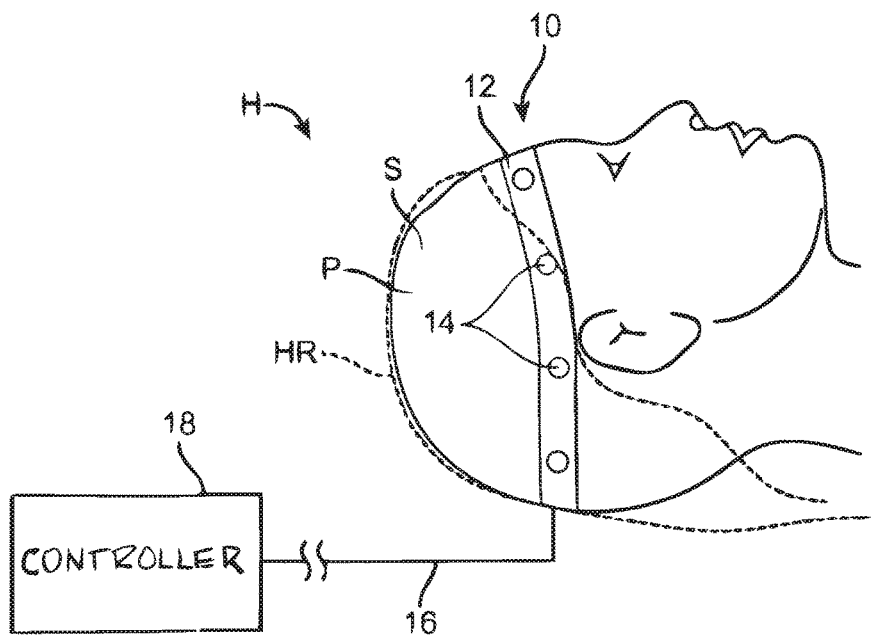
FIG. 1 illustrates a side view of a patient with an electrode carrier system configured as a headband.

The electrode carrier system 10 may generally comprise a backing 12 shown in the side view of FIG. 1 which illustrates the carrier system 10 secured around the head H of patient P. The backing 12 is shown configured as a headband in this variation although the carrier system 10 may be incorporated into any number of other platforms or positioning mechanisms for maintaining the electrodes against the patient body. The backing 12 is shown configured as a headband in this variation and the individual electrode assemblies 14 are spaced apart from one another so that when the headband is positioned upon the patient's head H, the electrode assemblies 14 are aligned optimally upon the head H for receiving EEG signals. The electrode carrier system 10 may have each of the electrodes assemblies 14 electrically coupled via corresponding conductive wires 16 extending from the backing 12 and coupled, e.g., to a controller and/or output device 18. Although in other variations, the electrodes assemblies 14 may be coupled to the controller and/or output device 18 wirelessly.

The controller and/or output device 18 may generally comprise any number of devices for receiving the electrical signals such as electrophysiological monitoring devices and may also be used in combination with any number of brain imaging devices, e.g., fMRT, PET, NIRS, etc. In one particular variation, the electrode embodiments described herein may be used in combination with devices such as those which are configured to receive electrical signals from the electrodes and process them.

The electrodes assemblies 14, as described herein, may be positioned upon the backing 12 to quickly enable conductive contact with the underlying skin while allowing for patient comfort such as when the patient P is reclined, as shown, with the back or side of their head H resting upon a surface without discomfort from the electrodes 14.

One challenge in ensuring that the individual electrodes 14 make sufficient contact with the underlying skin is the presence of hair HR on the scalp S of the patient P. The electrode carrier assemblies of the present disclosure as described herein enable rapid reliable electrical contact on individual electrode assemblies through the hair HR and with scalp surface without having to remove the hair.

Figure 2:
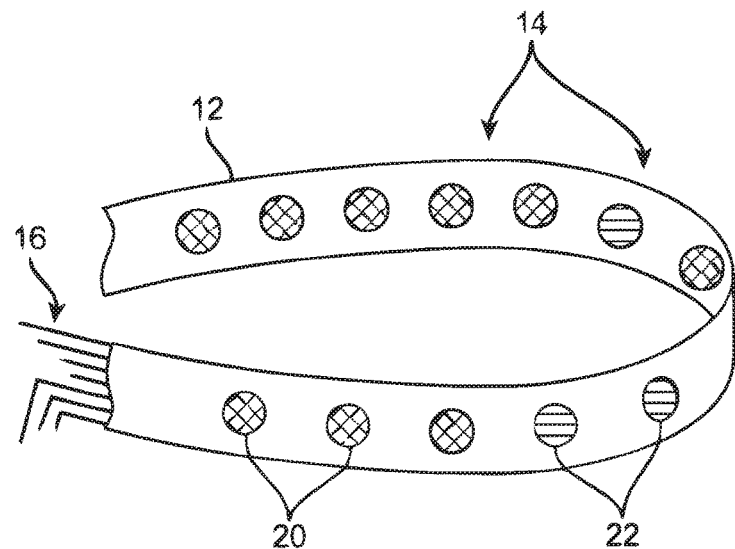
FIG. 2 illustrates a perspective view of one variation of the electrode carrier system where individual electrodes may be configured to indicate whether adequate contact is made with the underlying skin surface.

FIG. 2 shows an example where each of the electrodes 14 may also incorporate visual indicators such as one or more light emitting diodes (LEDs). When sufficient electrical contact is achieved, the LED on a particular electrode 14 may emit a light of a first color 20, e.g., green, but if an electrode 14 has not achieved sufficient electrical contact, it may emit a light of a second color 22, e.g., red. Alternatively, a single color LED may be used where sufficient contact may be indicated by steady illumination of the LED and insufficient contact may be indicated by a blinking LED. In other variations, an electrode may include, e.g., a piezoelectric transducer, eccentrically loaded weight coupled to a motor, etc., to provide for a vibration or other haptic response to indicate whether the electrode 14 has sufficient electrical contact with the underlying skin. In this manner, the electrodes 14 may efficiently provide direct indication of electrical contact rather than having to review a separate controller or indicator.

Figure 3A:
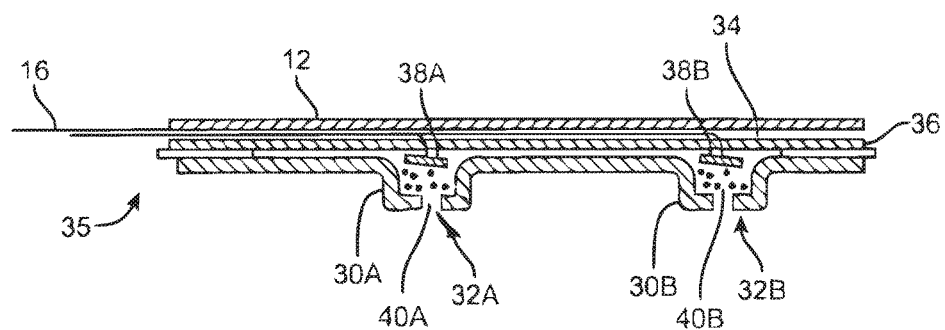
FIG. 3A illustrates a detail cross-sectional side view of another variation of the electrode carrier system where each of the electrodes may be encased or surrounded by a pressure release reservoir.

Turning now to the electrode configurations, FIG. 3A illustrates a cross-sectional detail side view of one variation of an electrode carrier system 35 where the electrodes 32A and 32B may be enclosed within a reservoir which is pre-filled with a conductive gel or fluid. Each electrode 38A, 38B may be configured into a flattened or atraumatic configuration which is contained within a respective reservoir 30A, 30B and each reservoir 30A, 30B may be formed of any number of flexible materials, e.g., silicone, polyurethane, rubber, etc., which can readily collapse. The electrodes 38A, 38B may be coupled via conductive wires 16 passing through a lumen 34 defined through the backing 12 separated from the electrodes by a substrate 36. Each reservoir 30A, 30B may also respectively define one or more openings 32A, 32B through which the conductive gel or fluid may be expelled.

Once the platform 12 has been situated over the patient's head H, the user may press upon each of the reservoirs 30A, 30B such that the conductive fluid or gel 40A, 40B flows through the openings 32A, 32B and onto the skin of the patient P. The conductive fluid or gel 40A, 40B expelled through the openings may maintain fluid communication between the skin surface and the respective electrodes 38A, 38B such that the detected electrical signals may be transmitted from the skin and to the electrodes 38A, 38B. Moreover, because of the flexibility of the reservoirs 30A, 30B, once the conductive fluid or gel 40A, 40B has been expelled into contact with the skin surface, the backing 12 may lie flat against the skin surface so that the patient P may comfortably lay their head upon a surface while still maintaining electrical contact with the electrodes 38A, 38B.

Figure 3B:
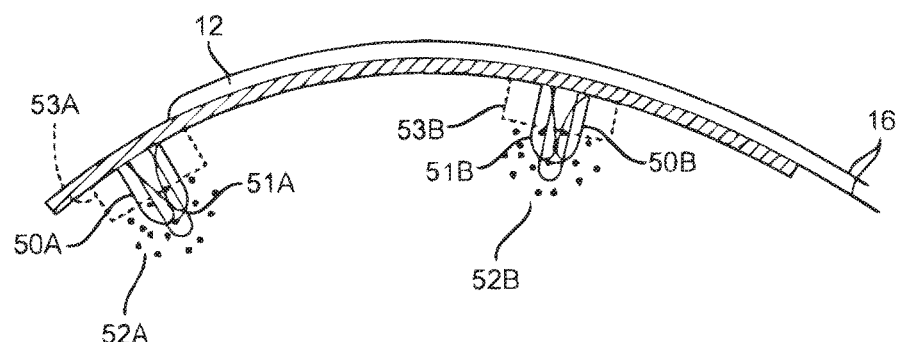
FIG. 3B illustrates a detail cross-sectional side view of another variation where the electrodes may be formed by one or more loops of conductive wire or ribbons.

FIG. 3B shows a side view of another electrode carrier system 35 where a pair electrode assemblies 50A, 50B may include one or more loops of conductive wire or ribbon 51A, 51B which are able to readily bend or flex against a skin surface. Some or all of the electrode assemblies 50A, 50B may include a pressure release reservoir (shown in broken lines 53A and 53B) for containing a conductive fluid or gel 52A, 52B, as described above, around each of the wire or ribbon electrodes 51A, 51B so that the conductive fluid or gel 52A, 52B may be expelled around and within the one or more loops to ensure a conductive path between the loops and the scalp. Alternatively, rather than using the pressure release reservoir, an amount of conductive fluid or gel may be simply placed upon the electrode assemblies 50A, 50B prior to placement against the patient's skin surface. Each of the wire or ribbon electrodes 51A, 51B may be electrically connected via conductive wires 16, and because the wire or ribbon electrodes 51A, 51B will preferably have a thin diameter or width, they may easily pass through the patient's hair and into contact with the scalp surface even when they bend or flex.

Figure 3C:
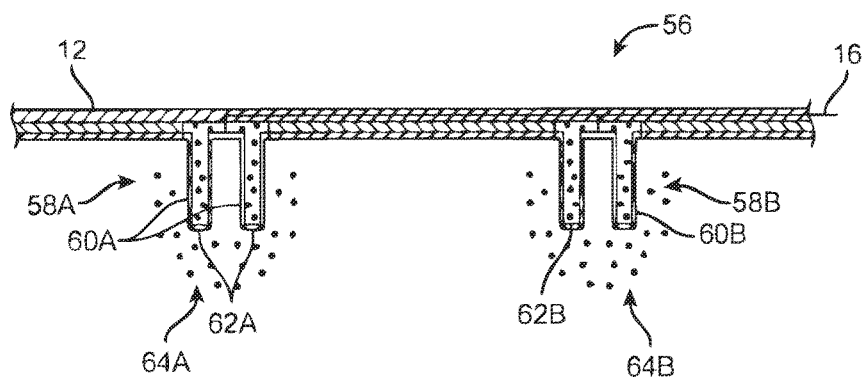
FIG. 3C illustrates a detail cross-sectional side view of another variation where each of the electrodes may be formed by one or more conductive tubes which define conduits.

FIG. 3C shows a side view of another variation of an electrode carrier system 56 having a plurality of electrode assemblies 58A and 58B each of which may include one or more tubular members 60A, 60B which may extend perpendicularly or at an angle from an inner surface (the surface that contacts the patient's scalp) of the backing 12. The tubular members 60A, 60B may define a lumen therethrough with an opening 62A, 62B defined at each distal end. Each of the tubular members 60A, 60B may be fabricated from a conductive metal which may retain its tubular shape when in use or which may be sufficiently thin and flexible to bend or yield when placed against the patient's skin surface. Alternatively, the tubular members 60A, 60B may be fabricated from a flexible material which is coated or layered with a conductive material such that the members retain their flexibility. In either case, a conductive fluid or gel 64A, 64B may be either contained within the tubular members 60A, 60B or they may be retained within a pressure release reservoir, as described above but not shown in FIG. 3C, surrounding or in proximity to each electrode. Because the tubular shape of the electrodes, they may readily pass through the patient's hair, if present, and into contact against the skin surface while maintaining electrical contact. The tubular members 60A, 60B may be arranged in tandem pairs, as shown, or may be arranged in a triangular, rectangular, or circular pattern when there are three, four, or more tubular members in a single electrode assembly 58A, 58B.

Figure 4A:
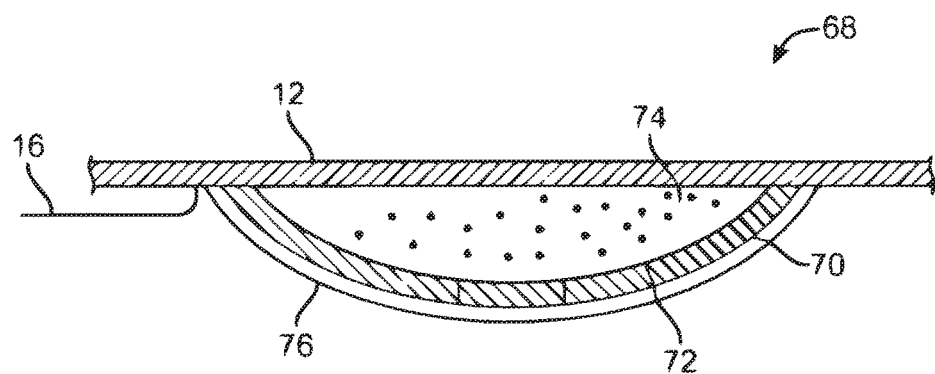
FIGS. 4A, 4B, and 4C illustrate cross-sectional side views of yet another variation where each electrode may include a compressible reservoir having one or more openings.
Figure 4B:
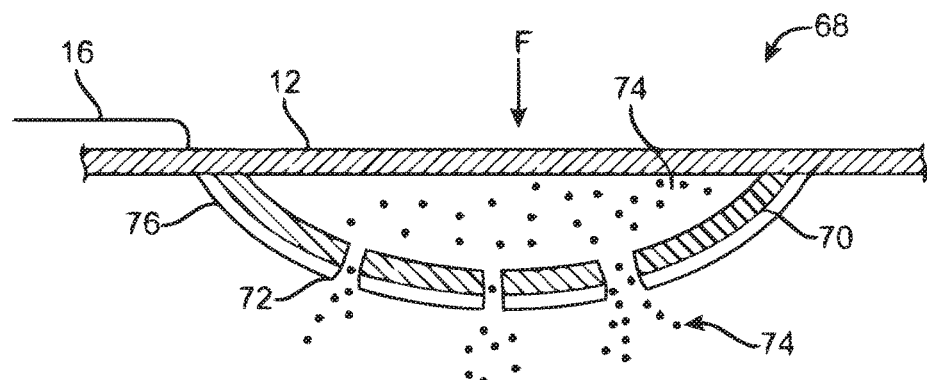
Figure 4C:
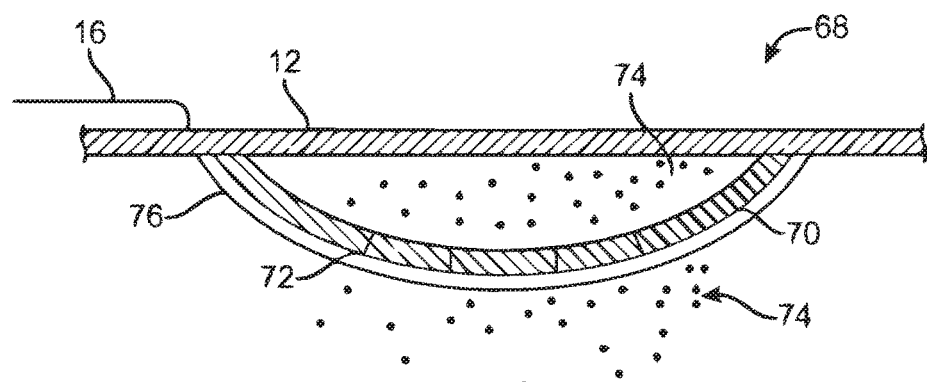

Referring to FIGS. 4A-4C, a further embodiment of an electrode carrier system 68 includes a pressure release reservoir 70 filled with a conductive fluid or gel 74. The reservoir 70 may be formed of a flexible material, e.g., silicone, polyurethane, rubber, a hydrogel, an elastomeric polymer, etc. The walls of the reservoir may be made from a conductive elastomer, e.g. rubber or silicone mixed with a portion of graphite, graphene, carbon nanotubes, etc. In embodiments where the walls of the reservoir are flexible, the reservoir may be resiliently collapsible, such that the reservoir returns to its previous shape after a force is applied. The reservoir extends from a backing 12 to form a curved or arcuate structure with one or more openings 72 defined over an interior of the reservoir 70. These openings 72 typically remain in a closed state until a force F is applied to the reservoir 70 and/or backing 12 to cause an electrically conductive fluid or gel 74 contained within the interior of the reservoir to escape through the openings 72, as shown in FIG. 4B, and into contact with an outer surface of the reservoir 70 and form an electrically conductive path to underlying skin surface. A layer of conductive material 76 is electrically coupled to conductive wire(s) 16 and may be formed over a portion or the entire outer surface of the reservoir 70. Electrical contact with the skin surface may be achieved by applying force F to the backing 12 or reservoir 76, as shown in FIG. 4B, to extrude or otherwise release the fluid or gel 74 from the interior of the reservoir 70 and out onto the conductive material 76 and skin as shown in FIG. 4C, where the openings 72 return to their closed state after the force F is removed.

Figure 5A:
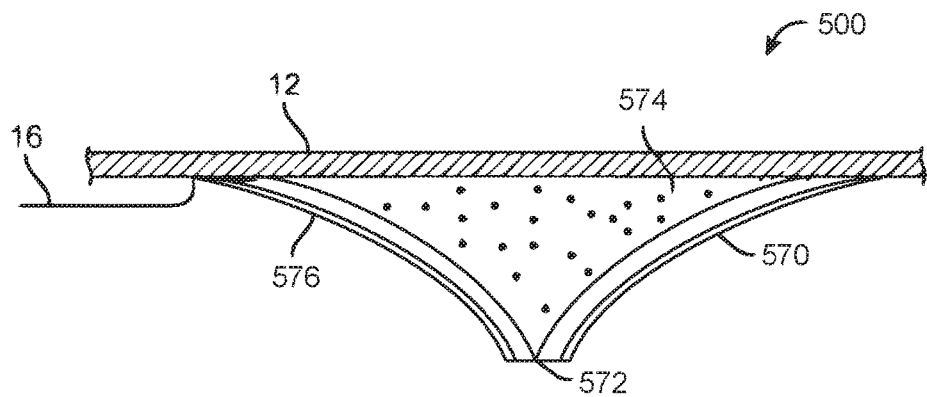
FIGS. 5A, 5B, and 5C illustrate cross-sectional side views of yet another variation where each electrode may include a compressible reservoir with a conical shape.
Figure 5B:
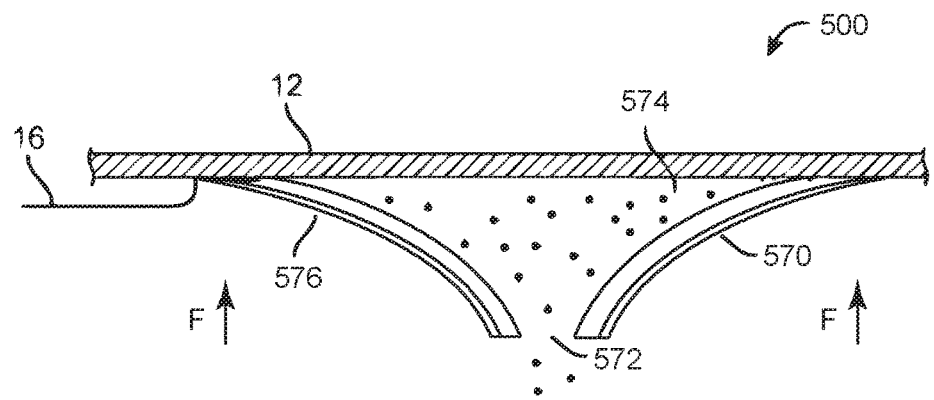
Figure 5C:
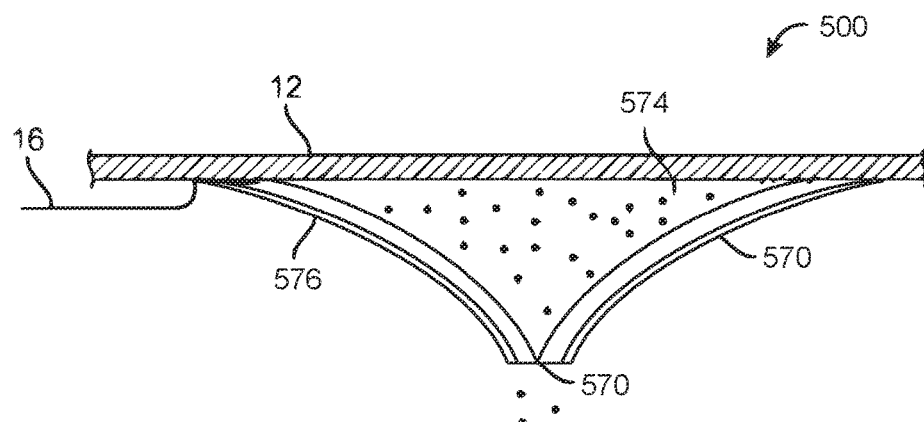

FIGS. 5A-5C illustrate an embodiment of a pressure release reservoir with a conical reservoir. Pressure release reservoir system 500 may include an interior reservoir 570 filled with a conductive fluid or gel 574. The reservoir 570 may be formed of a flexible material, e.g., silicone, polyurethane, rubber, a hydrogel, an elastomeric polymer, etc. The walls of the reservoir may be made from a conductive elastomer, e.g. rubber or silicone mixed with a portion of graphite, graphene, carbon nanotubes, etc. In embodiments where the walls of the reservoir are flexible, the reservoir may be resiliently collapsible, such that the reservoir returns to its previous shape after a force is applied. The reservoir extends from a backing 12 to form a conical structure with a single opening 572 in a distal end of the reservoir 570. The opening 572 typically remains in a closed state until a force F is applied to the reservoir 570 and/or backing 12 to cause an electrically conductive fluid or gel 574 contained within the interior of the reservoir to escape through the opening 572, as shown in FIG. 5B, and into contact with an outer surface of the reservoir 570 and form an electrically conductive path to underlying skin surface. In embodiments where the reservoir may be made from an insulating material, a layer of conductive material 576 is electrically coupled to conductive wire(s) 16 and may be formed over a portion or the entire outer surface of the reservoir 570. Electrical contact with the skin surface may be achieved by applying force F to the backing 12 or reservoir 570, as shown in FIG. 5B, to extrude or otherwise release the fluid or gel 574 from the interior of the reservoir 570 and out onto the skin as shown in FIG. 5C, where the openings 572 return to their closed state after the force F is removed.

Figure 6A:
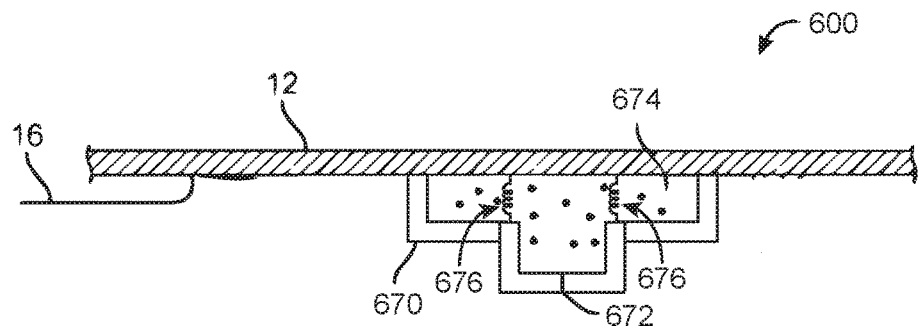
FIGS. 6A, 6B, and 6C illustrate cross-sectional side views of yet another variation where each electrode may include a compressible reservoir which may compress telescopically.
Figure 6B:
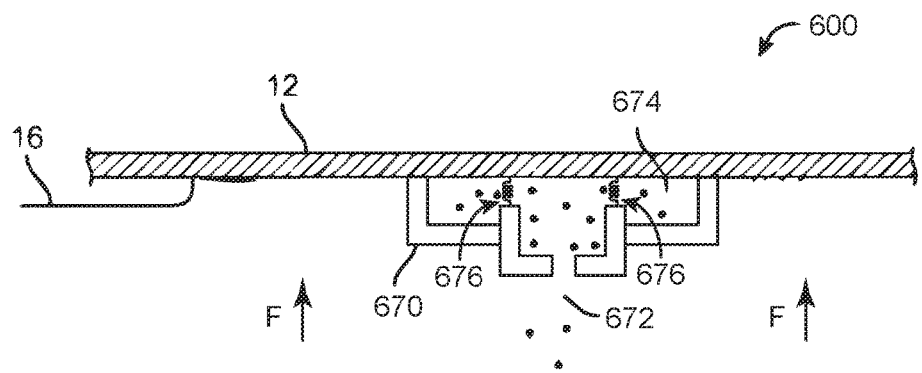
Figure 6C:
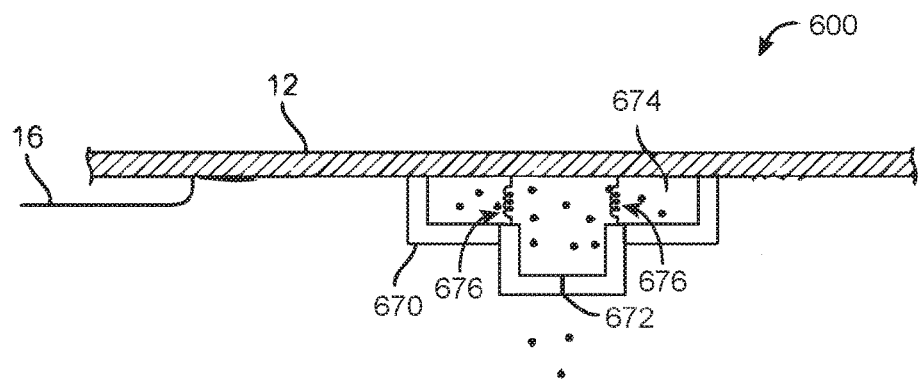

FIGS. 6A-6C illustrate an embodiment of a pressure release reservoir where the reservoir may compress telescopically. Pressure release reservoir system 600 may include an interior reservoir 670 filled with a conductive fluid or gel 674. The reservoir 670 may be formed of a flexible material, e.g., silicone, polyurethane, rubber, a hydrogel, an elastomeric polymer, etc. The walls of the reservoir may be made from a conductive elastomer, e.g. rubber or silicone mixed with a portion of graphite, graphene, carbon nanotubes, etc. In embodiments where the walls of the reservoir are flexible, the reservoir may be resiliently collapsible, such that the reservoir returns to its previous shape after a force is applied. The reservoir extends from a backing 12 to form two coaxial, telescoping cylinders with a single opening 672 in a distal end of the reservoir 670. In the illustrated embodiment, the telescoping elements of the reservoir 670 may be actuated by pressure changes in the chamber. Alternatively, the inner telescoping element may be spring-loaded or otherwise resiliently compressible relative to the outer telescoping element in order to provide restoring force after the reservoir is compressed. For example, one or more spring elements 676 may be internally positioned between the telescoping elements of the reservoir 670 to bias the telescoping elements apart by a desired distance; alternatively or in combination, a resiliently compressible material may be positioned between the telescoping elements of the reservoir 670 for the same purpose, and the resiliently compressible material may comprise a thermoplastic elastomer, a rubber material, a compressible foam, a compressible open-celled foam, a silicone-based material, to name a few. The opening 672 typically remains in a closed state until a force F is applied to the reservoir 670 and/or backing 12 to cause an electrically conductive fluid or gel 674 contained within the interior of the reservoir to escape through the opening 672, as shown in FIG. 6B, and into contact with an outer surface of the reservoir 670 and form an electrically conductive path to underlying skin surface. Electrical contact with the skin surface may be achieved by applying force F to the backing 12 or reservoir 670, as shown in FIG. 6B, to extrude or otherwise release the fluid or gel 674 from the interior of the reservoir 670 and out onto the conductive material 676 and skin as shown in FIG. 6C, where the openings 672 return to their closed state after the force F is removed.

Figure 7:
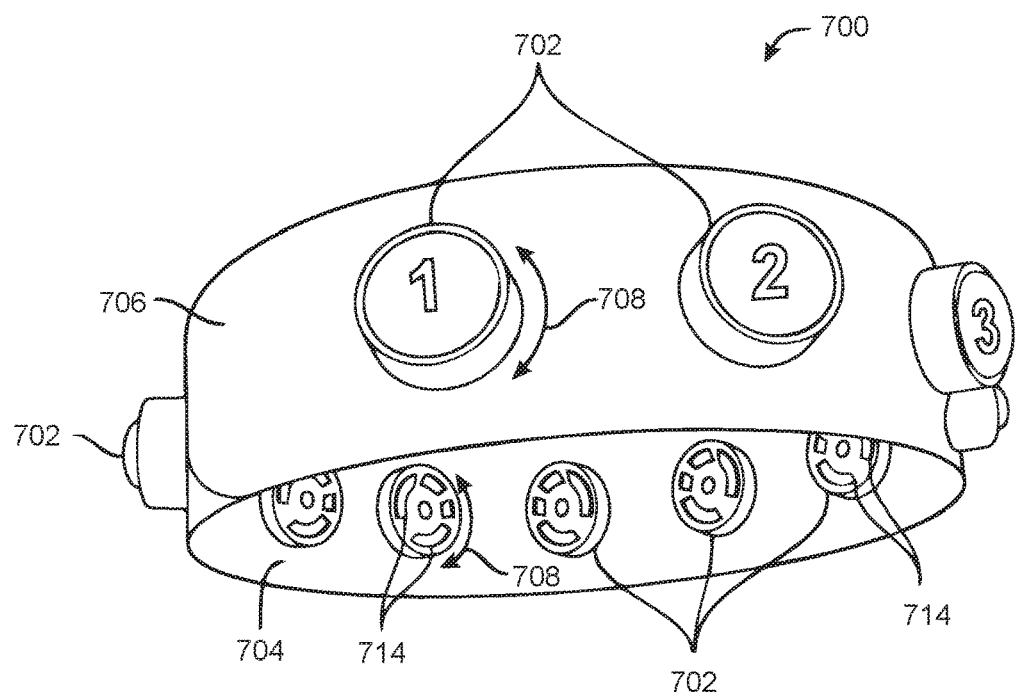
FIG. 7 illustrates an electrode carrier system of the present disclosure comprising a headband having a plurality of electrode assemblies distributed over a perimeter thereof.

Referring now to FIG. 7, an electrode carrier system 700 constructed in accordance with the principles of the present disclosure includes an elongated backing 704, typically in the form of a headband or other headgear, having a plurality of electrode assemblies 702 distributed along a perimeter thereof. The elongated backing 704 will typically have overlapping ends 706 which may be adjustably attached when the elongated backing is placed over a patient's head, generally as shown in FIG. 1 above, such that the electrode carrier system 700 may be wearable by patients across a wide range of head sizes. The overlapping ends may be attached using any conventional method, such as with Velcro® hook and loop fasteners.

The electrode assemblies 702 are preferably rotatably mounted so that a user can manually rotate them back and forth as shown by arrows 708 so that the patient's skin can be gently abraded after the elongated backing has been placed over the scalp and select electrode assemblies 702 are placed in contact with the patient's skin. In particular, it may be desirable to perform such manual abrasions immediately prior to dispensing the electrically conductive fluid or gel as will be described in more detail here and below. In other instances, the abrasion can be performed while dispensing the electrically conductive fluid or gel and/or after dispensing the electrically conductive fluid or gel. Alternatively or in combination, the electrically conductive fluid or gel itself may be at least partially abrasive and/or include abrasive elements to facilitate abrading the skin by movement of the electrode assemblies 702 and/or other elements. Examples of abrasive elements to be included in the electrically conductive fluid or gel may include particles of silica or silicon oxide, aluminum oxide, pumice, clay, lanolin, jojoba oil, to name a few. A commercially available abrasive conductive fluid or gel may comprise Nuprep® Skin Prep Gel available from Weaver and Company of Aurora, Colo.

Electrode assembly 702 may comprise embodiments of electrode assemblies 800, 900, 1000, 1100, and 1200 and may be incorporated into electrode carrier system 700 in accordance with aspects of the disclosure are presented in FIGS. 8A-12C. Electrode carrier system 700 may be used with a single embodiment of an electrode assembly (e.g. all electrode assemblies may comprise assembly 800). Alternatively, multiple embodiments of electrode assemblies may be used at various locations on a scalp. For instance, an electrode assembly comprising a flat contact surface, such as assembly 1200, may be used on a patient forehead and another assembly may be better suited in a location covered with hair, such as assembly 800. Electrode carrier system 700 may comprise embodiments 1300, 1400, 1500, and 1600 electrode assemblies comprising scalp preparers. In embodiments where a scalp preparer is a secondary tool, a scalp preparer may rotatably mounted in place of electrode assembly 702 and may subsequently be removed after the scalp is prepared. After preparation an electrode assembly 702 may be mounted.

Figure 8A:
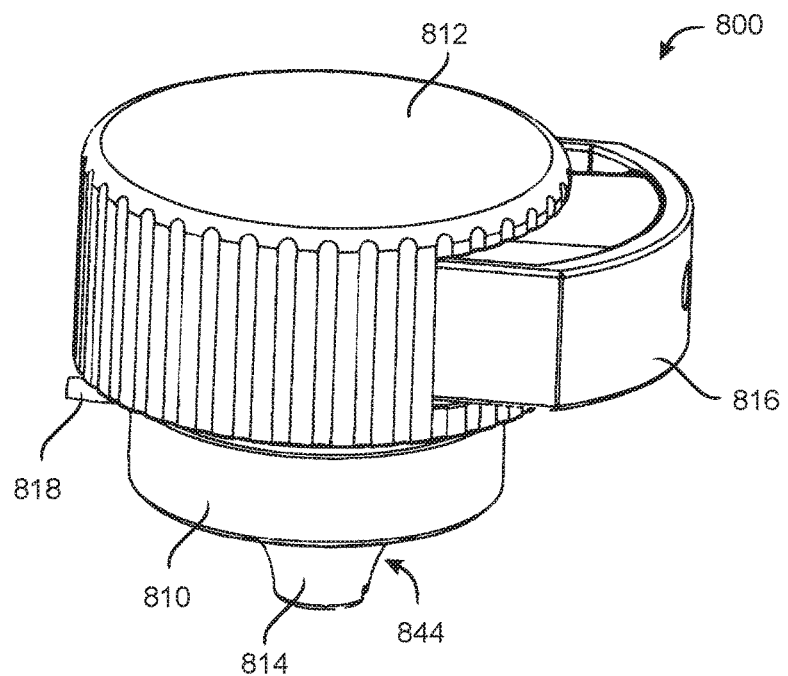
FIGS. 8A, 8B, and 8C show a perspective view, a section view, and a bottom view, respectively, of an electrode assembly which may comprise a plunger to activate dispensing of a conducting fluid or gel.
Figure 8B:
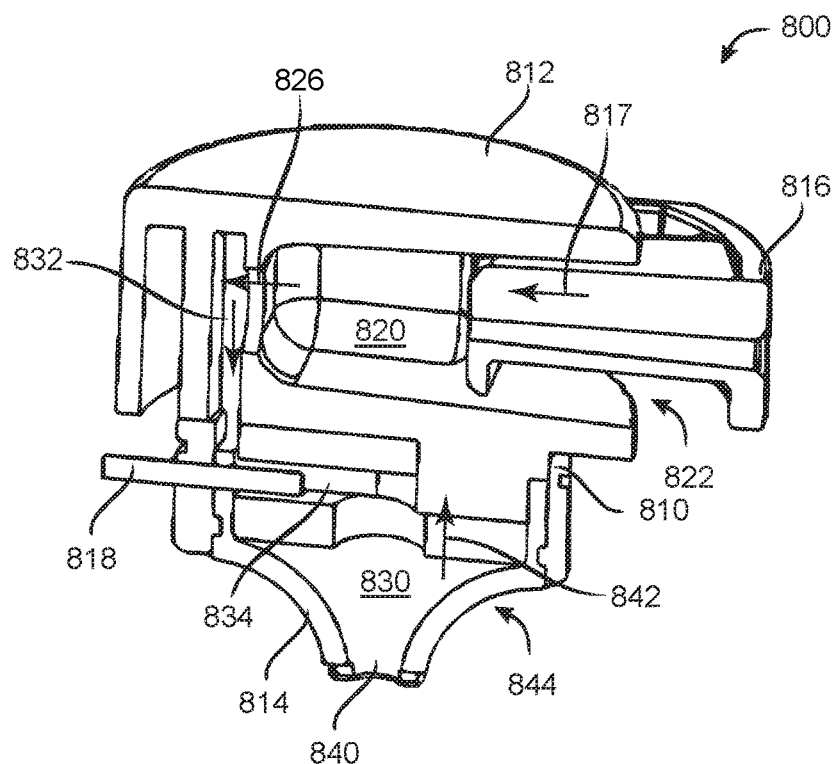
Figure 8C:
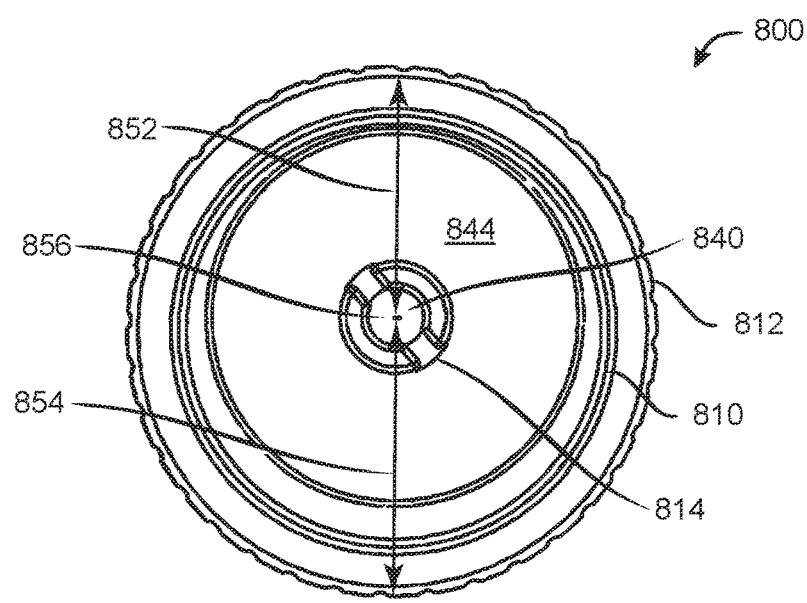

FIGS. 8A-8C show electrode assembly 800 which may comprise a plunger to activate dispensing of a conducting fluid or gel, in accordance with some embodiments. As shown in FIG. 8A, the electrode assembly 800 will typically include a lower body portion or base 810, an upper body portion or cap 812, and one or more at least partially collapsible or compressible body portion 814. Upper body portion 812 and lower body portion 810 may be rigid. A plunger 816 is configured to enter a chamber 824 within the upper body portion 812 through an opening 822. A sealed dispensing container, such as a cartridge or sealed dispensing container 820 holds the electrically conductive fluid or gel and is configured to be constrained within the chamber 824 while the plunger 816 extends readily outwardly from the upper body portion 812, i.e. is in its non-depressed configuration.

Once the sealed dispensing container 820 is placed in the chamber 824, the plunger 816 can be positioned so that a leading edge is adjacent one side of the sealed dispensing container. By pressing the plunger 816 in the direction of arrow 817, the electrically conductive fluid or gel within the sealed dispensing container 820 may be pressurized causing a portion of the container to pass through the dispensing hole 826. As additional pressure is applied with the plunger 816 the portion of the chamber within the dispensing hole 826 may rupture and cause the electrically conductive fluid or gel to flow into a vertical passage 832 within the upper body portion 812, as in FIG. 8B. The electrically conductive fluid or gel may then come in contact with the electrically conductive terminal 818, and the electrically conductive fluid or gel may continue to flow through a horizontal passage 834 and on to an interior reservoir 830 of the compressible body portion 814, as seen in FIG. 8B. In some embodiments, when pressure or force is applied along arrow 842, such as from a patient head pressing resting against a hard surface or by tightening electrode carrier 700, compressible body portion 814 may collapse decreasing the volume of interior reservoir 830. Increase in pressure or force may cause flow of fluid or gel along the flow path. From interior reservoir 830, the liquid or gel may flow outwardly through channel or aperture 840 formed in the bottom of the compressible body portion 814 so that it may flow on to patient tissue in contact with the lower surface 844 of the compressible body portion 814.

Once the entire flow path from the vertical passage 832 through the channel 840 in the lower surface of the compressible body portion 814 is filled with electrically conductive fluid or gel, it will be appreciated that biological electrical current present in the region of the liquid or gel may be conducted to the electrically conductive terminal 818 which in turn is connected to a wire or other conductor present in the backing 704 of the electrical carrier system 700. The attachment of the wire or other conductor to the electrically conductive terminal 818 may be made in such a fashion that it can accommodate rotation of the electrode assembly relative to the elongated backing 704, as shown by arrow 708 and FIG. 7.

FIG. 8C shows a view of the bottom of electrode assembly 800, in accordance with some embodiments. The center 856 of channel or aperture 840 may be set a distance offset from the center of lower body portion 810. Arrows 852 and 854 together comprise a diameter of circular upper body portion 810 passing through the center 856 of channel or aperture 840. In the illustrated embodiment, arrow 852 may be shorter than arrow 854. Channel 840 may be offset from the center of the upper body portion such that when electrode assembly 800 is rotated the distal end of the channel may traverse a circle on the patient skin, providing an enlarged area for abrading skin in comparison to the channel or aperture 840 being concentric with the lower body portion 810. The distal end of the compressible body portion may prepare a surface of the skin of a patient.

Figure 9A:
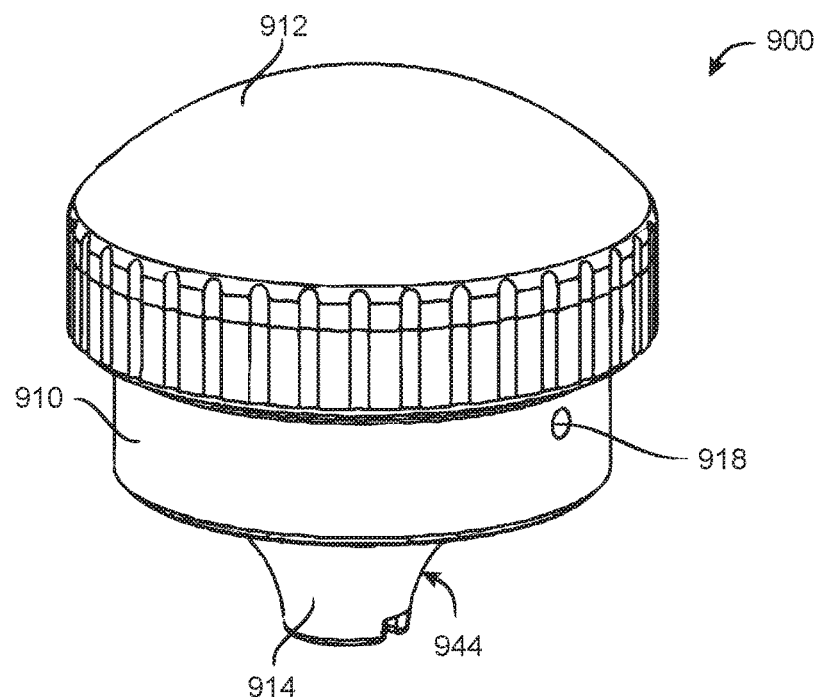
FIGS. 9A, 9B, and 9C show a perspective view, a section view, and a bottom view, respectively, of an electrode assembly which may comprise a depressible top surface or button to activate dispensing of a conducting fluid or gel.
Figure 9B:
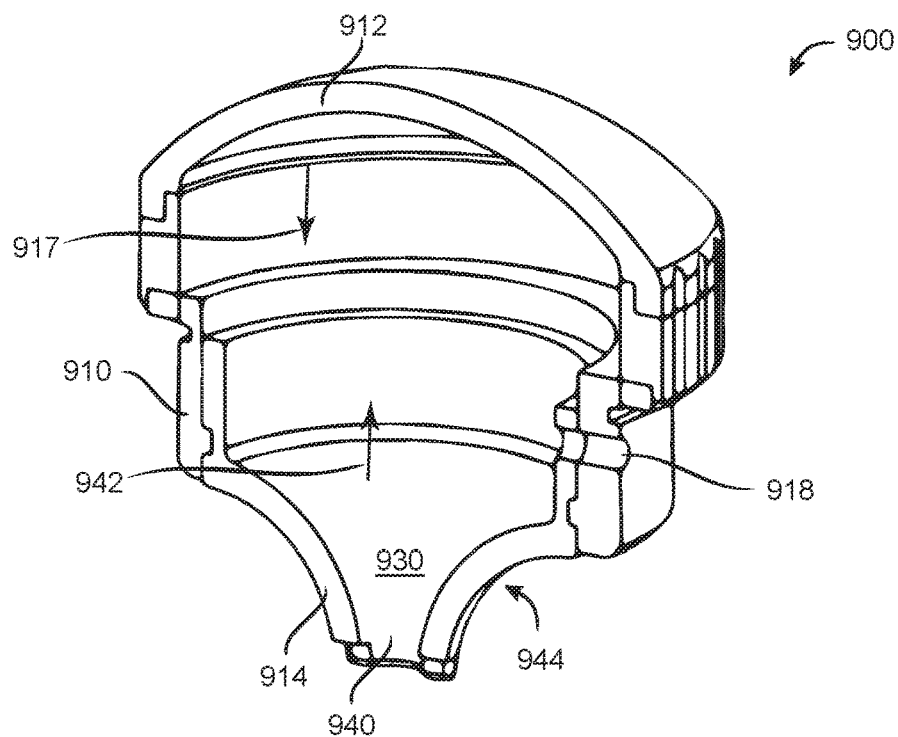
Figure 9C:
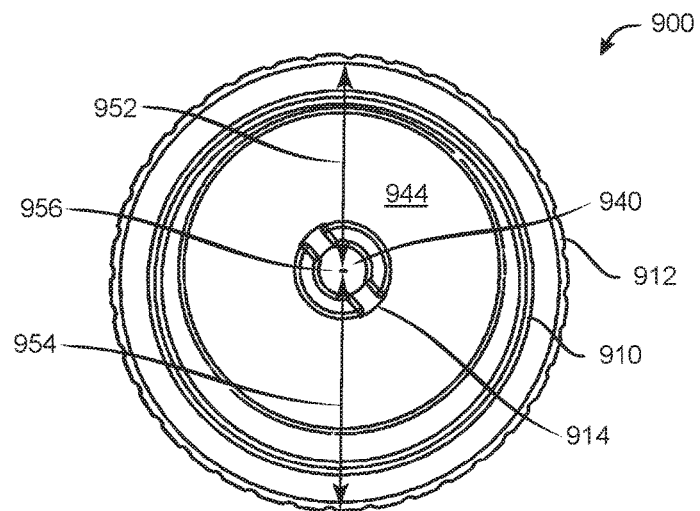

FIGS. 9A-9C show electrode assembly 900 which may comprise a depressible top surface or button to activate dispensing of a conducting fluid or gel, in accordance with some embodiments. As shown in FIG. 9A, the electrode assembly 900 will typically include a lower body portion or base 910, an upper body portion or depressible top surface 912, and one or more at least partially collapsible or compressible body portion 914. Lower body portion 910 may be rigid. The dome of depressible top surface 912 may be elastomeric. As shown in FIG. 9B by pressing the depressible top surface 912 in the direction of arrow 917, the electrically conductive fluid or gel within the interior reservoir 930 may be pressurized. The interior reservoir 930 may be a resiliently collapsible reservoir as described above and herein, optionally with a conical shape. In some embodiments, when pressure or force is applied along arrow 942, such as from a patient head pressing resting against a hard surface or by tightening electrode carrier 700, compressible body portion 914 may collapse decreasing the volume of interior reservoir 930. Increase in pressure or force may cause flow of fluid or gel along the flow path. As additional pressure is applied with the depressible top surface, the electrically conductive fluid or gel flows outwardly through channel or aperture 940 formed in the bottom of the compressible body portion 914 so that it may flow on to patient tissue in contact with the lower surface 944 of the compressible body portion 914.

Once the entire flow path through the channel 940 in the lower surface of the compressible body portion 914 is filled with electrically conductive fluid or gel, it will be appreciated that biological electrical current present in the region of the liquid or gel may be conducted to the electrically conductive terminal within slot 918 which in turn may be connected to a wire or other conductor present in the backing 704 of the electrical carrier system 700. The attachment of the wire or other conductor to the electrically conductive terminal within slot 918 may be made in such a fashion that it can accommodate rotation of the electrode assembly relative to the elongated backing 704, as shown by arrow 708 and FIG. 7.

FIG. 9C shows a view of the bottom of electrode assembly 900, in accordance with some embodiments. The center 956 of channel or aperture 940 may be set a distance offset from the center of lower body portion 910. Arrows 952 and 954 together comprise a diameter of circular upper body portion 910 passing through the center 956 of channel or aperture 940. In the illustrated embodiment, arrow 952 may be shorter than arrow 954. Channel 940 may be offset from the center of the upper body portion such that when electrode assembly 900 is rotated the distal end of the channel may traverse a circle on the patient skin, providing an enlarged area for abrading skin in comparison to the channel or aperture 940 being concentric with the lower body portion 910. The distal end of the compressible body portion may prepare a surface of the skin of a patient.

Embodiments of electrode assemblies 1000, 1100, and 1200 which may be incorporated into electrode carrier system 700 in accordance with aspects of the disclosure may comprise an adaptor for an external dispenser of the conductive fluid or gel. External dispensers may comprise a syringe, a manual squeeze tube, a roller squeeze tube, etc.

Figure 10A:
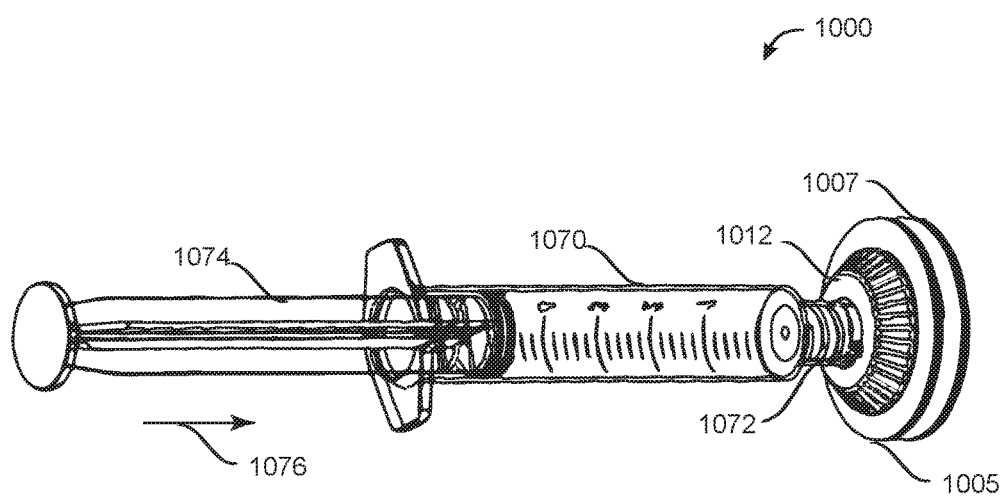
FIG. 10A shows a perspective view of an electrode assembly which may comprise a screw interface with an external disperser of a conductive fluid or gel.
Figure 10B:
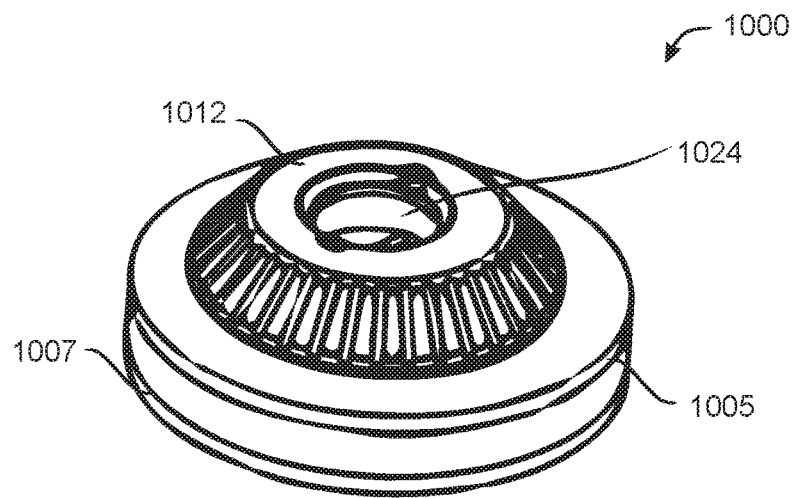
FIGS. 10B, 10C, and 10D show a perspective view, a section view, and a bottom view of the electrode assembly of FIG. 10A.

FIGS. 10A-10F show electrode assembly 1000 which may comprise a screw interface with an external dispenser of conductive fluid or gel. FIG. 10A shows an electrode assembly coupled to an external dispenser. FIG. 10B shows an electrode assembly decoupled from an external dispenser and a screw adaptor. The electrode assembly 1000 may be removably coupled to an external dispenser 1070 such as a syringe. The electrode assembly 1000 typically comprises a lower body portion or base 1010, an upper body portion or cap 1012, and one or more at least partially collapsible or compressible body portions 1014. In the illustrated embodiment, electrode assembly 1000 comprises skirt elements 1005 and 1007. The skirt elements may distribute force from a compressible body portion to a wider surface area, which may increase patient comfort. Skirt elements 1005 and 1007 may be coaxial with the body portion 1010 of the electrode assembly 1000. Skirt elements 1005 and 1007 may comprise a large surface area. Such a surface area may increase contact between a patient skin and electrode assembly 1000. Additionally, such a surface area may provide an increased contact area between a conductive liquid or gel and an electrode assembly and/or between a conductive liquid or gel and a patient skin. Additionally, the smaller profile of electrode assembly 1000 may decrease the amount of acute direct pressure that may directed from a pillow or bed, for instance, through the electrode assembly to the patient's scalp and may increase a patient's comfort during use. Skirt elements may comprise a flexible material. Additionally or alternatively, skirt elements may secure electrode assembly 1000 to an electrode carrier system 700. In other embodiments, the skirt elements may be removably coupled to the electrode body. In some embodiments, the skirt element(s) may be spring-loaded or loaded with a resiliently compressible material relative to the electrode body such that the skirt element(s) may telescope relative to the electrode body. The resiliently compressible material may comprise a thermoplastic elastomer, a rubber material, a compressible foam, a compressible open-celled foam, a silicone-based material, to name a few examples.

The external dispenser may comprise a means of dispensing a fluid or gel, such as a plunger 1074, which may be depressed along arrow 1076. In alternative embodiments, other means of actuation such a folding, twisting, or squeezing may be utilized to dispense a fluid or gel from a dispenser 1070. In the illustrated embodiments, dispenser 1070 comprises a first surface of screw interface 1072 (e.g. a Luer attachment), which may twist together with a corresponding second surface 1066. The first and second surfaces may comprise an embodiment of an adaptor which may couple an external dispenser 1070 to an electrode assembly 1000. Other embodiments may comprise a compression fitting, snap fitting, retaining rings, etc. The second surface of the screw interface 1066 may be removably coupled to the upper body portion 1012 of the electrode assembly 1000. In alternative embodiments, the second surface of the screw interface may be fixed relative to the upper body portion. In some embodiments, upper body portion 1012 and screw interface 1066 may be separate during manufacturing and fixed after initial assembly. In alternate embodiments, the screw interface 1066 may be removable between uses to enable cleaning of the electrode assembly 1000 via entrance aperture 1024, shown in FIG. 10B.

Figure 10C:
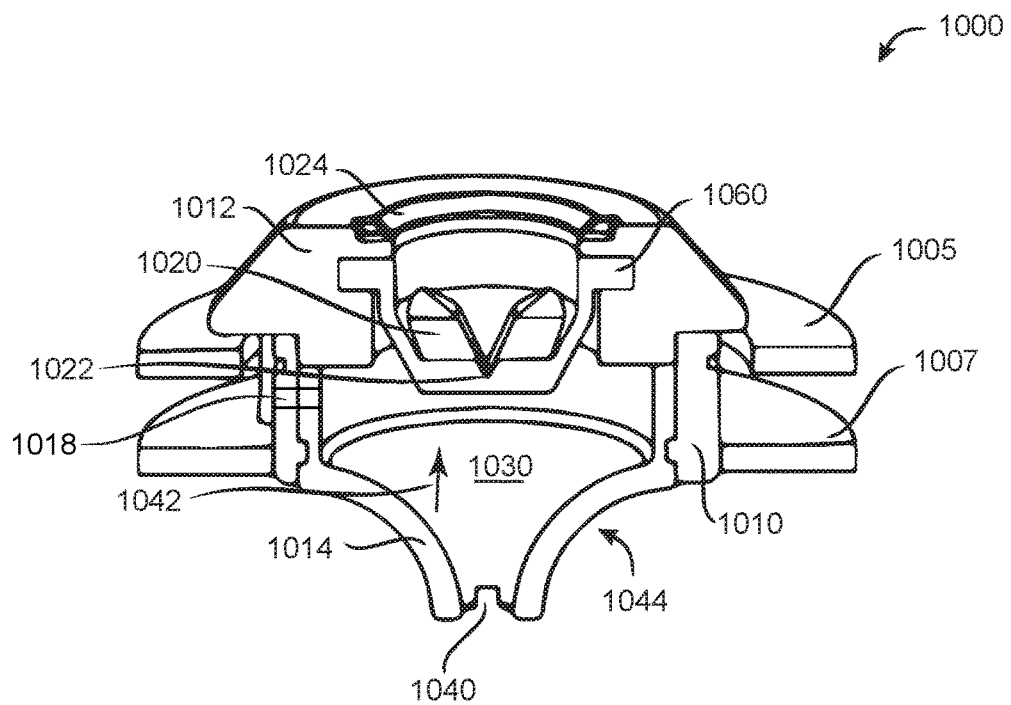
Figure 10D:
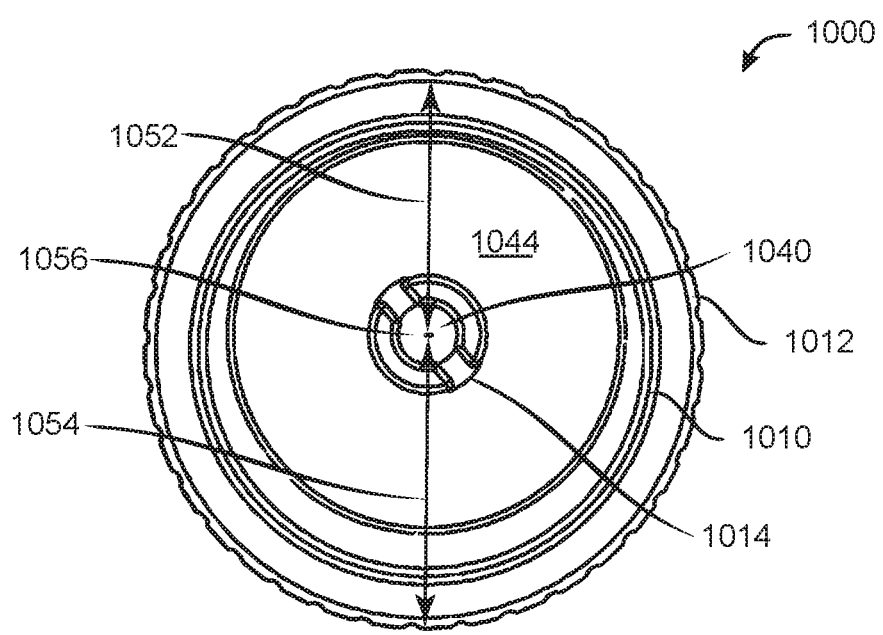
Figure 10E:
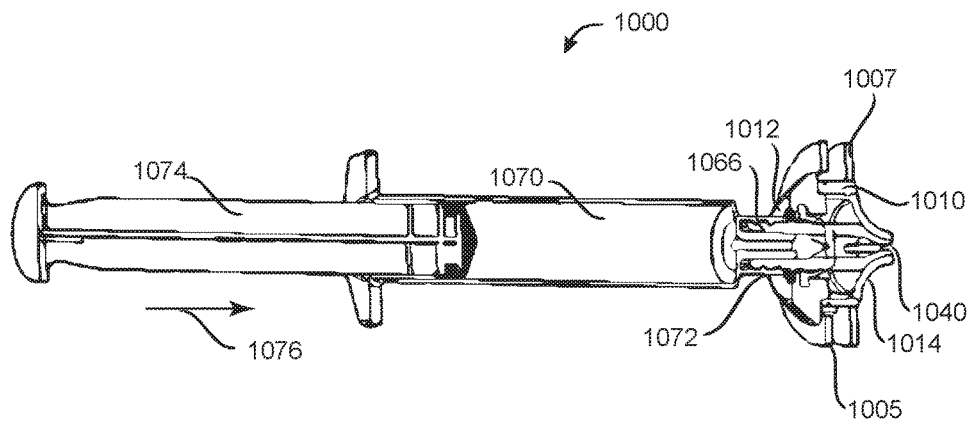
FIGS. 10E and 10F show a side section view and a magnified section view of the electrode assembly of FIG. 10A in use with the external dispenser.

As shown in FIG. 10E, second surface of the screw interface 1066 may comprise keyed or other mating-type features that facilitate scalp preparation which may require an increased mechanical transfer of force to be directed toward the scalp, such as during scalp preparation with rotation based actuation. Adding force directed towards the scalp during scalp preparation can be beneficial when the electrode assembly is used with electrode assembly designs that have collapsible, compressible, or telescoping bottom surfaces that are designed to not ordinarily apply much force to the patient's scalp by themselves. As shown in FIG. 10B, upper body portion 1012 may comprise a ridged or textured surface. In some embodiments, the electrode assembly can act as a knob that allows for additional skin preparation actuation and force application even when the electrode assembly tool is not being used to collect electrical data.

FIG. 10C shows a slice through electrode assembly 1000, in accordance with some embodiments. As shown in the illustrate embodiment, upper body portion 1012 and lower body portion 1010 may be rigid. In the illustrated embodiment, compressible body portion 1014 may be elastomeric. Electrode assembly 1000 may comprise an internal reservoir 1030. Internal reservoir 1030 may comprise electrically conductive fluid or gel. Optionally, upper body portion 1012 may comprise a valve 1020 to allow external filling and/or refilling of the conductive fluid or gel. Valve 1020 may be integrated with an adaptor 1060 which may connect with a screw interface 1066. In some embodiments, adaptor 1060 may be flexible. In alternate embodiments, upper body portion may comprise a restriction instead of a valve. Additionally or alternatively, the valve 1020 may prevent back flow of gel when pressure is increased inside of the internal reservoir. Valve 1020 may comprise a duck-bill valve, a cross-slit valve, a ball valve, a pinch valve, etc. The exit aperture 1022 may be open during filling and closed when an external dispenser is removed. The entrance aperture 1024 may be sized and shaped to interface with a wide variety of external dispensers known to one of skill in the art such as a syringe, a squeeze tube, etc. In some embodiments, the entrance aperture 1024 may be spring-loaded or otherwise provided with a resiliently compressible material to such that the external dispenser will need to be pushed toward the entrance aperture 1024 before dispensing the conductive fluid or gel, thereby minimizing risks of inadvertent dispensing.

The interior reservoir 1030 may be a resiliently collapsible reservoir as described above and herein, optionally with a conical shape. When pressure or force is applied along arrow 1042, such as from a patient head pressing resting against a hard surface or by tightening electrode carrier 700, compressible body portion 1014 may collapse decreasing the volume of interior reservoir 1030. As additional pressure is applied, the electrically conductive fluid or gel flows outwardly through channel or aperture 1040 formed in the bottom of the compressible body portion 1014 so that it may flow on to patient tissue in contact with the lower surface 1044 of the compressible body portion 1014.

Once the entire flow path through the channel 1040 in the lower surface of the compressible body portion 1014 is filled with electrically conductive fluid or gel, it will be appreciated that biological electrical current present in the region of the liquid or gel may be conducted to the electrically conductive terminal within slot 1018 which in turn is connected to a wire or other conductor present in the backing 704 of the electrical carrier system 700. The attachment of the wire or other conductor to the electrically conductive terminal may be made in such a fashion that it can accommodate rotation of the electrode assembly relative to the elongated backing 704, as shown by arrow 708 and FIG. 7.

FIG. 10D shows a view of the bottom of electrode assembly 1000, in accordance with some embodiments. The center 1056 of channel or aperture 1040 may be set a distance offset from the center of lower body portion 1010. Arrows 1052 and 1054 together comprise a diameter of circular upper body portion 1012 passing through the center 1056 of channel or aperture 1040. In the illustrated embodiment, arrow 1052 may be shorter than arrow 1054. Channel 1040 may be offset from the center of the upper body portion such that when electrode assembly 1000 is rotated the distal end of the channel may traverse a circle on the patient skin, providing an enlarged area for abrading skin in comparison to the channel or aperture 1040 being concentric with the lower body portion 1010. The distal end of the compressible body portion may prepare a surface of the skin of a patient, such for example as by mechanical abrasion.

FIG. 10E shows a slice through electrode assembly 1000 coupled to external dispenser 1070 of FIG. 10A, in accordance with some embodiments. External dispenser 1070 may comprise a reservoir to store a conductive fluid or gel. External dispenser 1070 may comprise an actuator 1074, such as a plunger, which when depressed along an arrow 1076 may cause fluid or gel to be dispensed into the reservoir of an electrode assembly 1030.

Figure 10F:
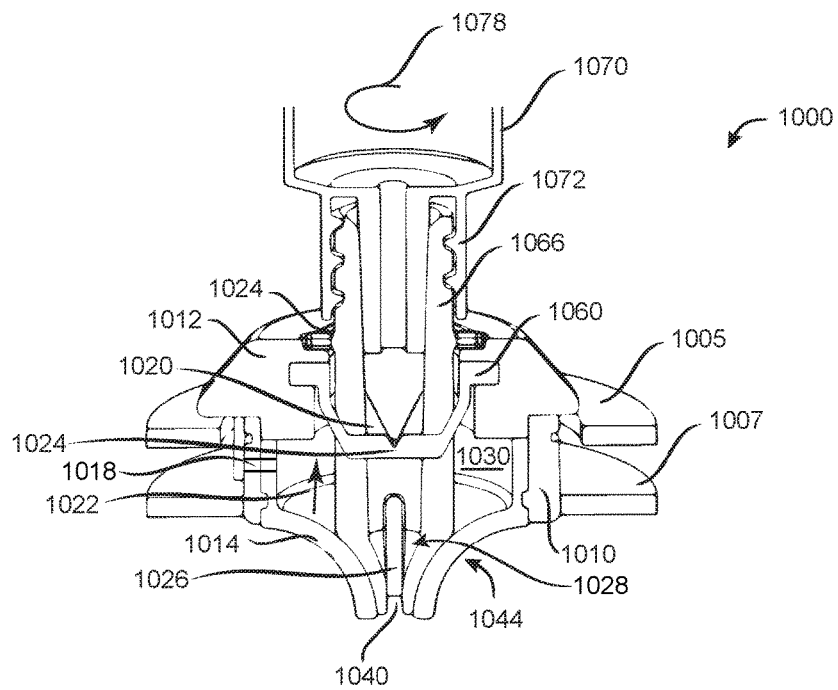

FIG. 10F shows a slice through electrode assembly 1000 comprising an adaptor with a screw interface 1066, in accordance with some embodiments. In some embodiments, adaptor 1060 and screw interface 1066 may be integrated into a single part; alternatively, adaptor 1060 and screw interface 1066 may be separate parts which may be press fit, glued, or otherwise removably or permanently affixed. External dispenser 1070 may be removably coupled to electrode assembly 1000 by rotation about an axis of the screw as shown by arrow 1078. In some embodiments, electrode assembly 1000 may comprise a an internal divider 1028 which may comprise open channels 1026 which may direct a conductive liquid or gel more evenly into reservoir 1030.

Figure 11A:
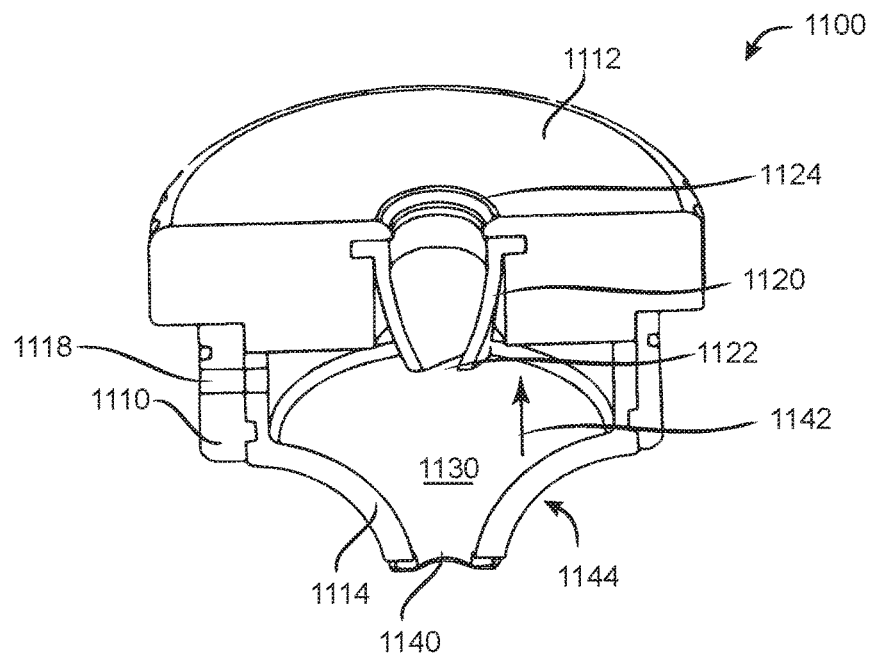
FIGS. 11A, 11B, and 11C show a section view, a perspective view, and a bottom view, respectively, of an electrode assembly which may comprise a duck-bill valve to interface with an external dispenser of the conductive fluid or gel.
Figure 11B:
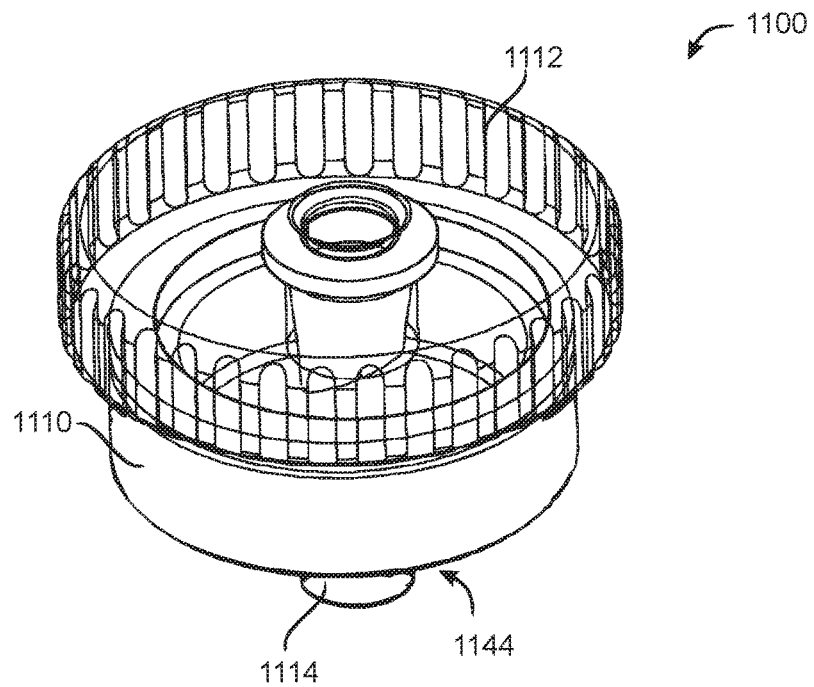
Figure 11C:
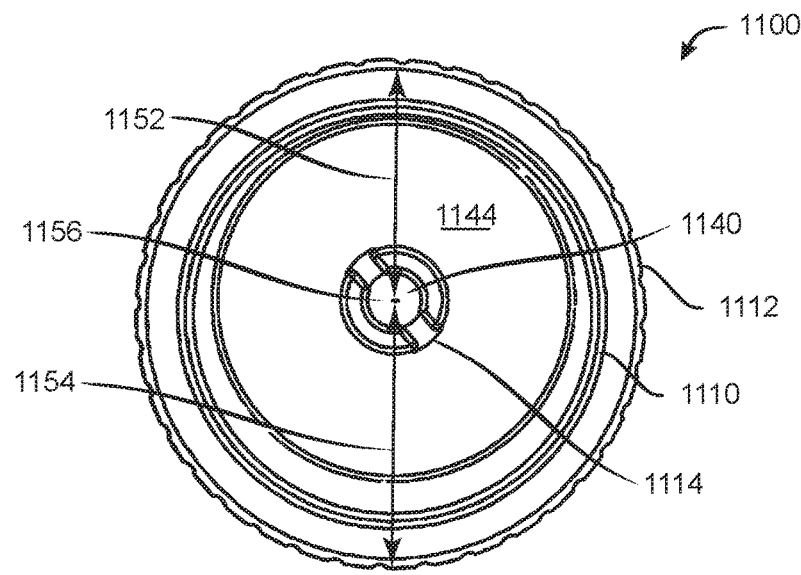

FIGS. 11A-11C show electrode assembly 1100 which may comprise a duck-bill valve to interface with an external dispenser of the conductive fluid or gel, in accordance with some embodiments. As shown in FIG. 11A, the electrode assembly 1100 will typically include a lower body portion or base 1110, an upper body portion or cap 1112, and one or more at least partially collapsible or compressible body portions 1114. Upper body portion 1112 and lower body portion 1110 may be rigid. In the illustrated embodiment, compressible body portion 1114 may be elastomeric. The valve 1120 may allow for repeated filling of the electrode with conductive gel to counteract gel evaporation or drying. Additionally, the valve may allow for additional skin preparation after a gel has been dispensed, which may be beneficial for extended collection and use.

As shown in FIG. 11A, an internal reservoir 1130 holds the electrically conductive fluid or gel. Upper body portion 1112 may comprise a valve 1120 to prevent allow external filling and/or refilling of the conductive fluid or gel. Additionally or alternatively, the valve 1120 may prevent back flow of gel when pressure is increased inside of the internal reservoir. Valve 1120 may comprise a duck-bill valve, a cross-slit valve, a ball valve, a pinch valve, etc. The exit aperture 1122 may be open during filling and closed when an external dispenser is removed. The entrance aperture 1124 may be sized and shaped to interface with a wide variety of external dispensers known to one of skill in the art such as a syringe, a squeeze tube, etc. In some embodiments, the entrance aperture 1124 may be spring-loaded or otherwise provided with a resiliently compressible material to such that the external dispenser will need to be pushed toward the entrance aperture 1124 before dispensing the conductive fluid or gel, thereby minimizing risks of inadvertent dispensing.

The interior reservoir 1130 may be a resiliently collapsible reservoir as described above and herein, optionally with a conical shape. When pressure or force is applied along arrow 1142, such as from a patient head pressing resting against a hard surface or by tightening electrode carrier 700, compressible body portion 1114 may collapse decreasing the volume of interior reservoir 1130. As additional pressure is applied, the electrically conductive fluid or gel flows outwardly through channel or aperture 1140 formed in the bottom of the compressible body portion 1114 so that it may flow on to patient tissue in contact with the lower surface 1144 of the compressible body portion 1114.

Once the entire flow path through the channel 1140 in the lower surface of the compressible body portion 1114 is filled with electrically conductive fluid or gel, it will be appreciated that biological electrical current present in the region of the liquid or gel may be conducted to the electrically conductive terminal within slot 1118 which in turn is connected to a wire or other conductor present in the backing 704 of the electrical carrier system 700. The attachment of the wire or other conductor to the electrically conductive terminal within slot 1118 may be made in such a fashion that it can accommodate rotation of the electrode assembly relative to the elongated backing 704, as shown by arrow 708 and FIG. 7.

FIG. 11C shows a view of the bottom of electrode assembly 1100, in accordance with some embodiments. The center 1156 of channel or aperture 1140 may be set a distance offset from the center of lower body portion 1110. Arrows 1152 and 1154 together comprise a diameter of circular upper body portion 1110 passing through the center 1156 of channel or aperture 1140. In the illustrated embodiment, arrow 1152 may be shorter than arrow 1154. Channel 1140 may be offset from the center of the upper body portion such that when electrode assembly 1100 is rotated the distal end of the channel may traverse a circle on the patient skin. The distal end of the compressible body portion may prepare a surface of the skin of a patient.

Figure 12A:
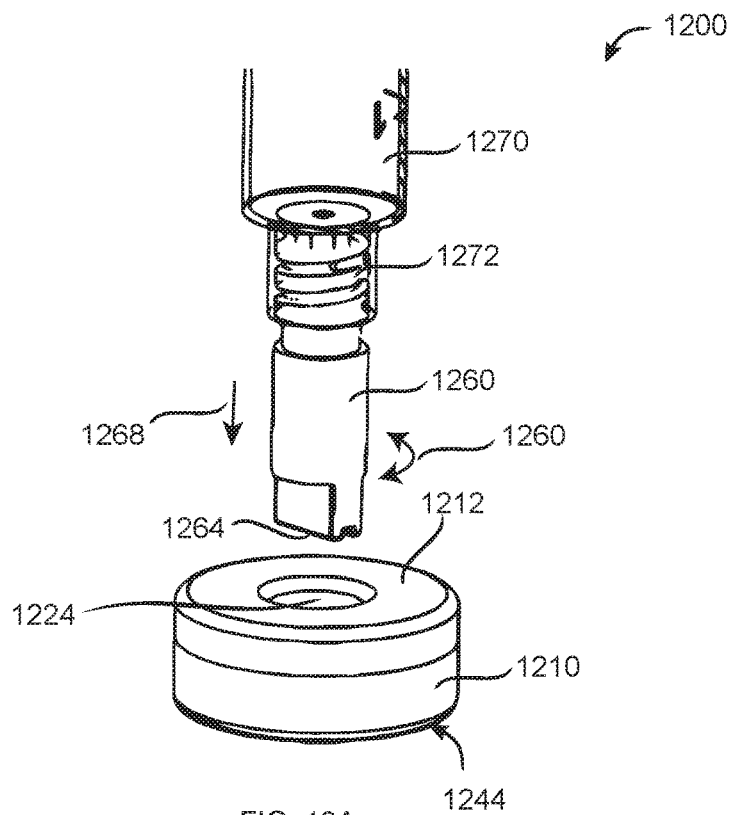
FIGS. 12A, 12B, and 12C show a perspective view, a section view, and a bottom perspective view, respectively, of an electrode assembly in use with an external gel dispenser having a scalp preparation element disposed thereon.
Figure 12B:
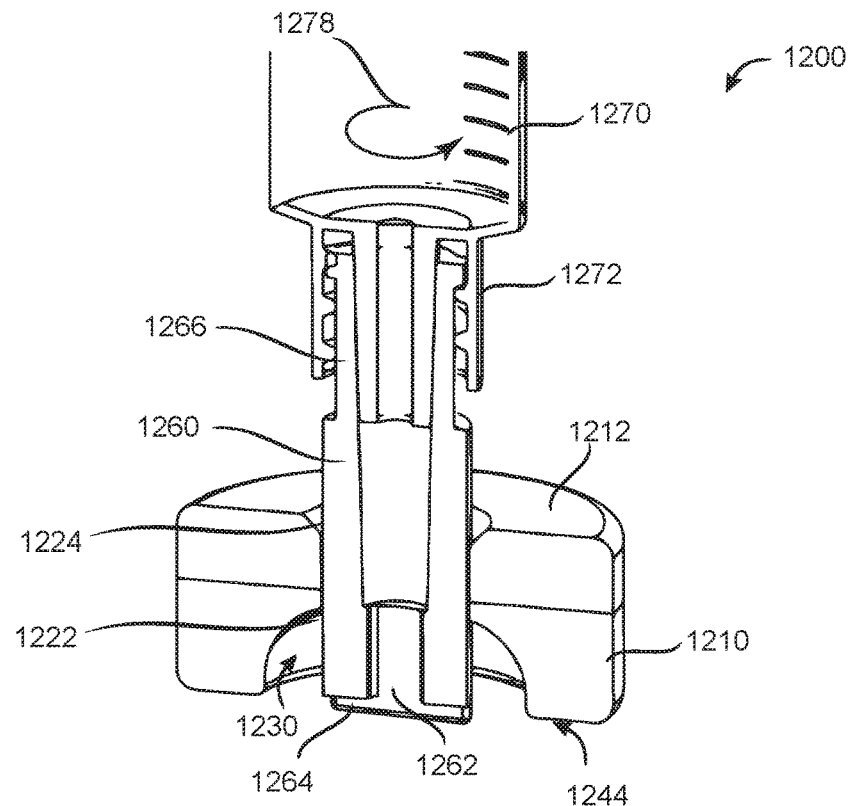
Figure 12C:
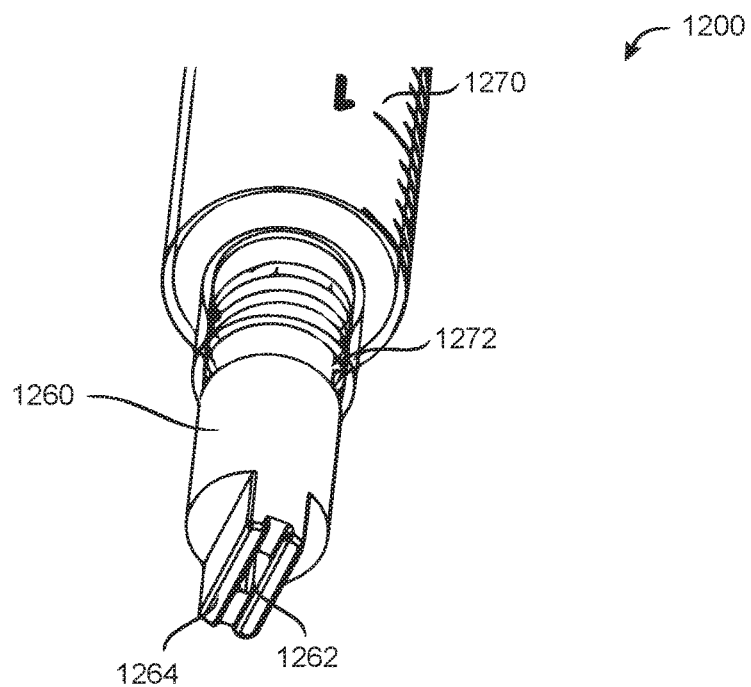

FIGS. 12A-12C shows an electrode assembly comprising a scalp preparer disposed on the external dispenser, in accordance with some embodiments. Electrode assembly 1200 may comprise an external dispenser which may make direct contact with a patient scalp for direct scalp preparation, with scalp preparing surfaces and features, and gel delivery. This may reduce the design requirements of the rest of the electrode assembly, which may function primarily to maintain contact between the electrode, conductive gel, and the scalp. The dispensed electrode gel may be filled and/or refilled as necessary. Additionally, the electrode material may be less rigid, for example, by using a sponge, foam, or soft rubber.

As shown in FIG. 12A, the electrode assembly 1200 will typically include a lower body portion 1210 and an upper body portion 1212. The upper body portion may comprise upper aperture 1224 into which an external dispenser 1270 may be inserted. The external dispenser may comprise a reservoir to store a conductive fluid or gel and a means of dispensing a fluid or gel, such as a plunger. In alternative embodiments, other means of actuation such a folding, twisting, or squeezing may be utilized to dispense a fluid or gel from a dispenser 1270. In the illustrated embodiments, dispenser 1270 may comprise a first surface of screw interface 1272 (e.g. a Luer attachment), which may couple to an adaptor 1260. The adaptor 1260 may be slidably inserted into the upper aperture on an axis along arrow 1268. The adaptor 1260 may additionally comprise an orifice 1264 on the distal end of the adaptor through which a conductive liquid or gel may be dispensed. The distal end of the adaptor may additionally comprise a scalp preparing surface. Twisting of the adaptor along arrow 1269 may actuate the scalp preparer.

FIG. 12B shows the external dispenser and adaptor of FIG. 12A after insertion into upper aperture 1224, in accordance with some embodiments. Upper aperture may be in fluid communication with a lower aperture 1222. The reservoir of the dispenser may be coupled to a central channel of adaptor 1260 which may allow fluid or gel to pass through an aperture 1262 of adaptor 1260. The lower body portion 1210 may comprise a bottom surface 1244 which may be conductive. Additionally, the lower body portion may comprise a cavity or reservoir 1230 which may receive a fluid or gel dispensed through lower aperture 1222. Increase in pressure from the dispenser may cause flow of fluid or gel along the flow path out of the dispenser and filling the reservoir. From reservoir 1230, the liquid or gel may flow outwardly through the bottom of the body portion so that it may flow on to patient tissue in contact with lower surface 1244. Electrode assembly 1200 may comprise an electrical terminal which in turn is connected to a wire or other conductor present in the backing 704 of the electrode carrier system 700. FIG. 12C show a view of the distal end of the adaptor 1260. The distal end may comprise an aperture 1262 and scalp preparing members 1264.

Embodiments of the present disclosure provide means of preparing a patient tissue to improve electrical contact. Elongate elements on the distal ends of various embodiments of electrode assemblies (e.g. compressible body portions of electrode assemblies 800, 900, 1000, and 1100) may allow electrical contact to be made through a patient's hair present on a scalp. In some embodiments, these elongate elements may comprise a plurality of protrusions or fingers. Optionally, the elongate elements may comprise containment features for containing conductive gel or fluid which has been disposed through the bottom opening. FIGS. 13A-16C show embodiments 1300, 1400, 1500, and 1600 of scalp preparers which may be used either as a separate prep tool or as examples, embodiments, and variations of a compressible body portion of electrode assemblies 800, 900, 1000, and 1200.

Use of a scalp preparer as a secondary tool may allow for a more comfortable electrode assembly to be used for longer term wear, for use lying down, or for more sensitive patients. Scalp preparers of the present disclosure may be movable relative to the body of the wearable sensor. In some embodiments, a scalp prepare may be one or more of rotated, translated, and pivoted relative to the electrode carrier assembly. Scalp preparers may prepare a scalp by clearing skin, hair, etc. which may be disruptive to electrical conduct with the scalp. In some embodiments, scalp preparers may comprise flexible elements to facilitate patient comfort. Such flexible elements may promote patient comfort for long term use. In alternative embodiments, scalp prepares may comprise rigid elements. In embodiments where the scalp prepare comprises rigid elements, a scalp preparer may be removably placed within an electrode carrier assembly. A scalp prepare may be used to prepare a scalp and then replaced with a more comfortable electrode assembly for longer term use.

Figure 13A:
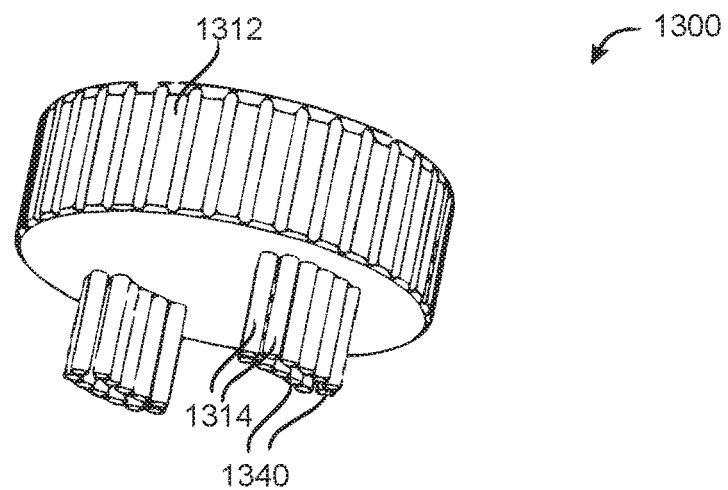
FIGS. 13A and 13B illustrate a perspective view and an exploded view, respectively, of an electrode assembly comprising a scalp preparer which may be interfaced with an external dispenser.
Figure 13B:
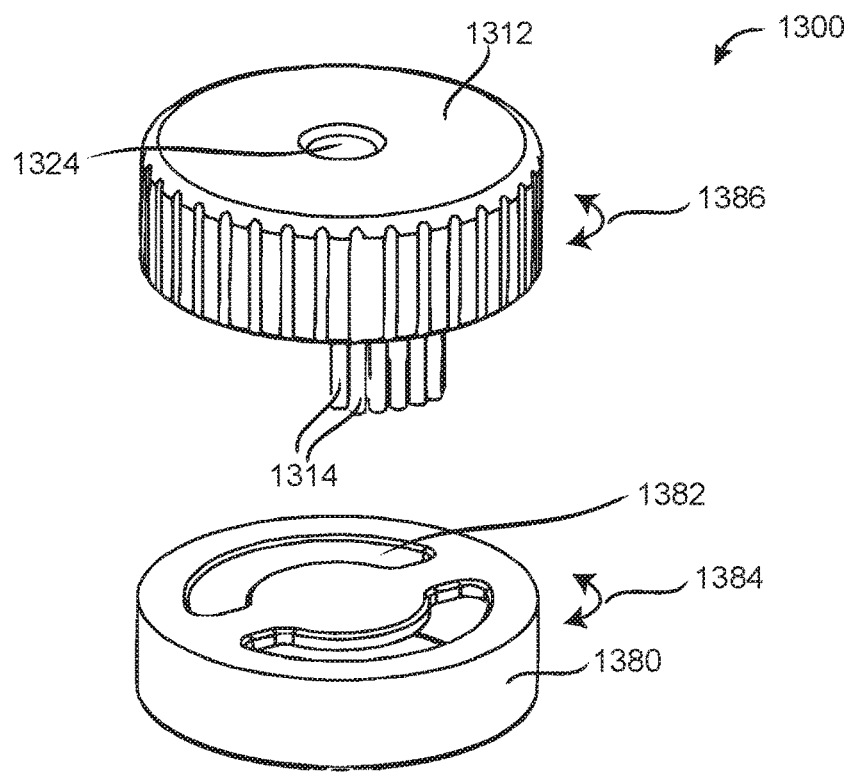

FIGS. 13A-13B illustrate an electrode assembly comprising a scalp preparer 1300 which may be interfaced with an external dispenser, in accordance with some embodiments. Optionally, in some embodiments scalp preparer 1300 is an embodiment of an electrode assembly, which may be integrated into an electrode carrier assembly of the present disclosure. FIG. 13A shows a bottom view of a scalp preparer comprising a body 1312 and elongate elements 1314. Elongate elements 1314 may be rigid, abrasive, or rigid and abrasive. In some embodiments, elongate elements 1314 are conductive. In some embodiments, elongate elements 1314 comprise apertures 1340 which may be fluidically coupled to a reservoir. While the illustrated example shows a single aperture in each elongate element. In alternative embodiments, the elongate elements may comprise a plurality of apertures. In some embodiments, the elongate elements may comprise a porous and/or spongy material. In embodiments where the elongate elements are conductive or comprise a conductive element, a porous and/or spongy material may increase the surface area of contact between the gel and the electrode to increase electrical contact. The reservoir may contain a conductive fluid or gel. Such a reservoir may be internal to the scalp preparer; however, in alternative embodiments, a conductive fluid or gel may be contained in an external dispenser, such as those described herein with respect to FIGS. 10A-E, 11A-C, 12A-C, and 13A-B. As disclosed elsewhere herein, the conductive fluid or gel may be at least partially abrasive and/or include abrasive elements.

FIG. 13B shows a top view of an electrode assembly comprising a scalp preparer 1300. Scalp preparer 1300 may comprise an entrance aperture 1324. Entrance aperture 1324 may be sized and shaped to interface with a wide variety of external dispensers known to one of skill in the art such as a syringe, a squeeze tube, etc. FIG. 13B also shows a carrier 1380 for assembly 1300. Carrier 1380 may removably coupled to an electrode carrier assembly and to a scalp preparer. Carrier 1380 comprises slot 1382. Elongate elements 1314 may be received by slot or stencil element 1382. The slot may allow embodiments of a scalp preparer to rotate relative to the carrier, which may, optionally, be fixed relative to the electrode carrier assembly. In some embodiments, the entrance aperture 1324 may be spring-loaded or otherwise provided with a resiliently compressible material to such that the external dispenser will need to be pushed toward the entrance aperture 1324 before dispensing the conductive fluid or gel, thereby minimizing risks of inadvertent dispensing.

Figure 14:
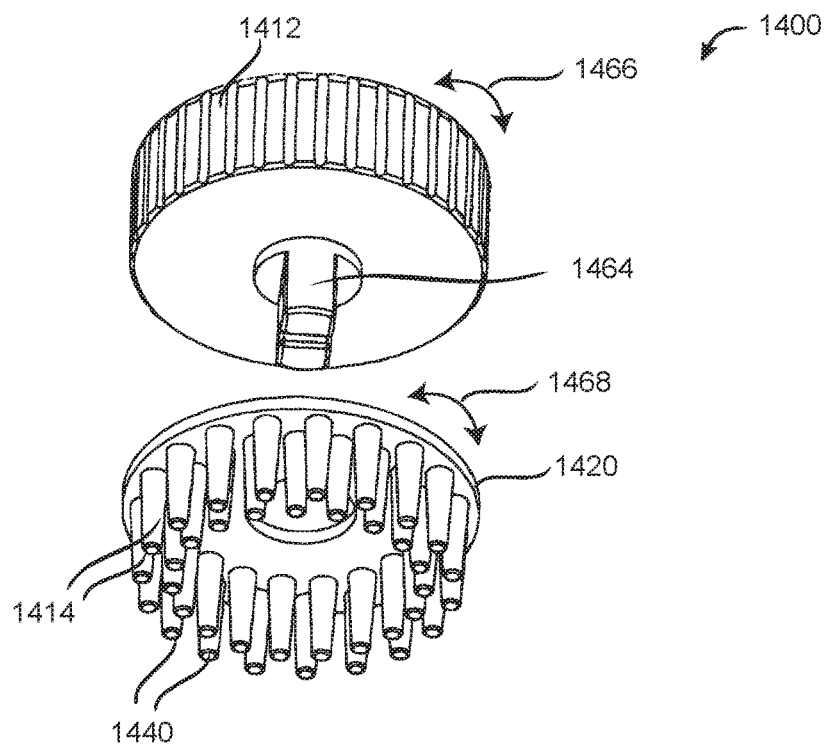
FIG. 14 illustrates an exploded view of an electrode assembly comprising a scalp preparer which may be interfaced with an external dispenser having a skin preparing surface.

FIG. 14 illustrates an electrode assembly comprising a scalp preparer 1400 which may be interfaced with an external dispenser having a skin preparing surface, in accordance with some embodiments. Optionally, in some embodiments scalp preparer 1400 is an embodiment of an electrode assembly, which may be integrated into an electrode carrier assembly of the present disclosure. FIG. 14 shows a bottom view of a scalp preparer comprising a body 1412 and a distal end of an external dispenser 1464. Distal end 1464 may comprise an embodiment, variation, or example of the external dispenser comprising a scalp preparing surface of FIG. 12A to FIG. 12C. Body 1412 may optionally comprise a reservoir which may contain a conductive liquid or gel. Such a reservoir may be internal to the scalp preparer; however, in alternative embodiments, a conductive fluid or gel may be contained in an external dispenser, such as those described herein with respect to FIGS. 10A-E, 11A-C, 12A-C, and 13A-B.

In some embodiments, scalp preparer 1400 comprises a bottom portion 1420. Bottom portion 1420 may comprise elongate elements 1414. Elongate elements 1414 may be rigid, abrasive, or rigid and abrasive. In some embodiments, elongate elements 1414 are conductive. In some embodiments, elongate elements 1414 comprise apertures 1440 which may be fluidically coupled to a reservoir. While the illustrated example shows a single aperture in each elongate element. In alternative embodiments, the elongate elements may comprise a plurality of apertures. In some embodiments, the elongate elements may comprise a porous and/or spongy material. In embodiments where the elongate elements are conductive or comprise a conductive element, a porous and/or spongy material may increase the surface area of contact between the gel and the electrode to increase electrical contact. In some embodiments body 1412 is rotated while bottom portion 1420 is moved. In alternative embodiments, body 1412 is moved while bottom portion 1420 is fixed. In some embodiments, both elements move together.

Figure 15:
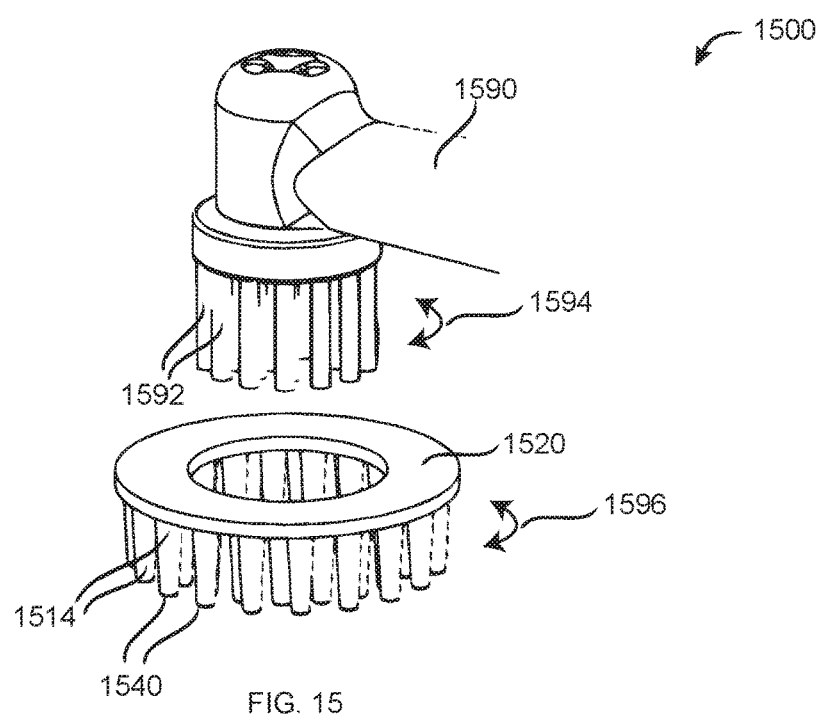
FIG. 15 illustrates an exploded view of an electrode assembly comprising a scalp preparer which may be interfaced with an external abrasive element.

FIG. 15 illustrates an electrode assembly comprising a scalp preparer 1500 which may be interfaced with an external abrasive element, in accordance with some embodiments. Optionally, in some embodiments, scalp preparer 1500 is an embodiment of an electrode assembly, which may be integrated into an electrode carrier assembly of the present disclosure, such as carrier assembly 700. In some embodiments, scalp preparer 1500 comprises a bottom portion 1520. Bottom portion 1520 may comprise elongate elements 1514. Elongate elements 1514 may be rigid, abrasive, or rigid and abrasive. In some embodiments, elongate elements 1514 are conductive. In some embodiments, elongate elements 1514 comprise apertures 1540 which may be fluidically coupled to a reservoir. While the illustrated example shows a single aperture in each elongate element. In alternative embodiments, the elongate elements may comprise a plurality of apertures. In some embodiments, the elongate elements may comprise a porous and/or spongy material. In embodiments where the elongate elements are conductive or comprise a conductive element, a porous and/or spongy material may increase the surface area of contact between the gel and the electrode to increase electrical contact. In some embodiments, external abrasive element 1590 is rotated while bottom portion 1520 is moved. External abrasive element may move relative to the bottom portion as indicated by arrows 1594. In alternative embodiments, external abrasive element 1590 is moved while bottom portion 1520 is fixed. In such embodiments, the bottom portion may move as indicated by arrows 1596. In some embodiments, both elements move together. As disclosed elsewhere herein, the conductive fluid or gel may be at least partially abrasive and/or include abrasive elements.

Figure 16A:
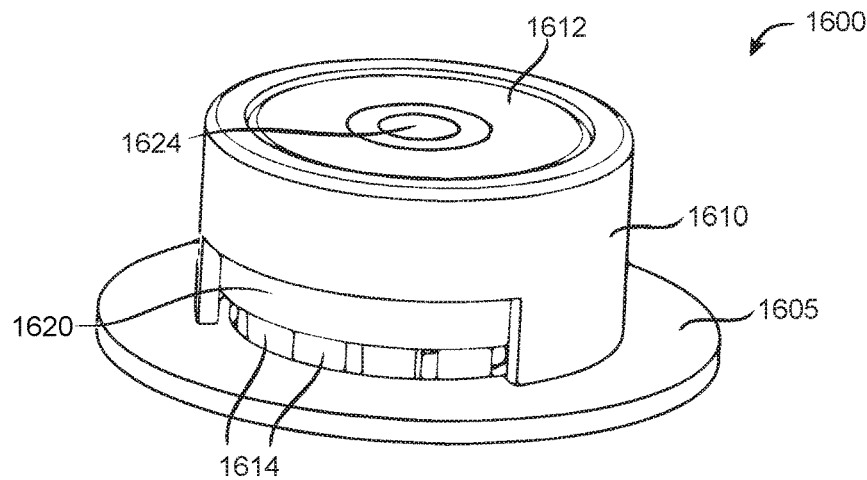
FIGS. 16A, 16B, and 16C illustrate perspective views of an electrode assembly comprising an adjustable structure which may additionally comprise scalp preparing elements.
Figure 16B:
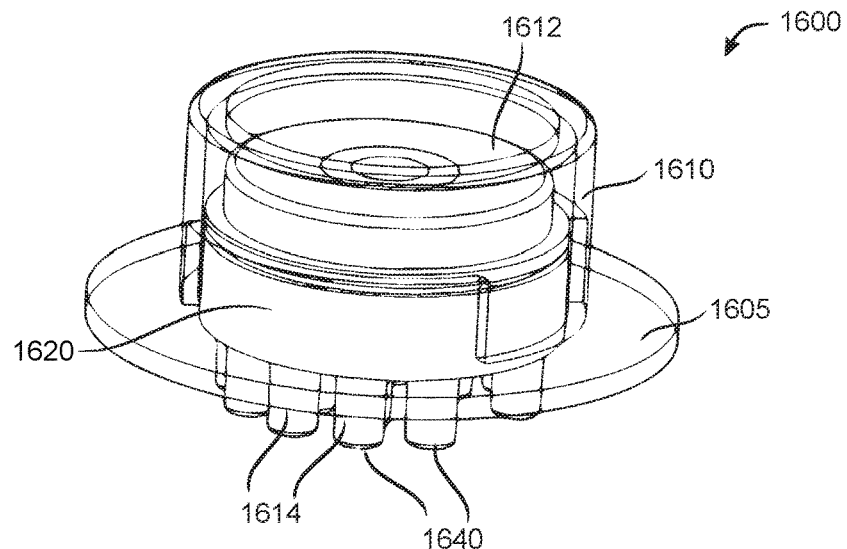
Figure 16C:
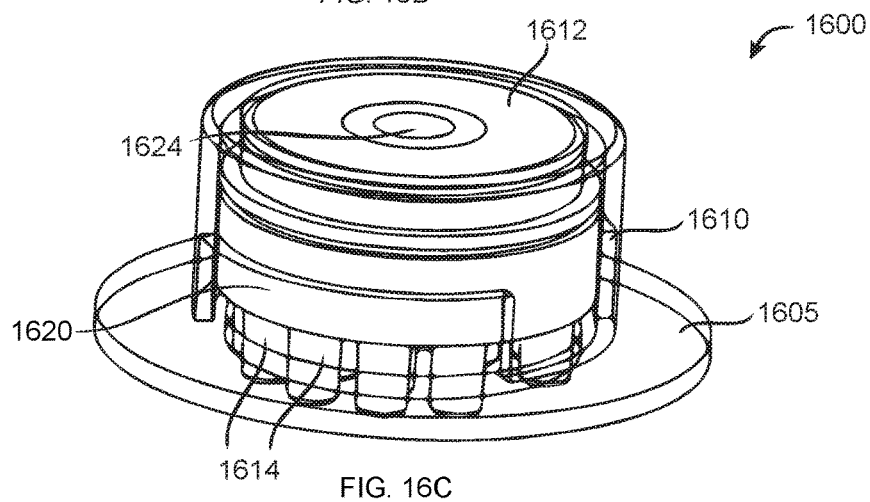

FIGS. 16A-16C illustrate an electrode assembly 1600 comprising an adjustable structure which may additionally comprise scalp preparing elements, in accordance with some embodiments. Optionally, in some embodiments, electrode assembly 1600 may be integrated into an electrode carrier assembly of the present disclosure. Electrode assembly 1600 may comprise structures, which may be external or internal, which may reduce the direct force that may be transmitted through the electrode body and its distal features to the patient scalp. Adjustable structures may increase patient comfort. Adjustable structures may comprise configurations which apply variable or constant force, may be spring-loaded, loaded with a resiliently compressible material which may act similarly to a spring (for example, a thermoplastic elastomer, a rubber material, a compressible foam, a compressible open-celled foam, a silicone-based material, to name a few), and/or adjusted mechanically. Adjustments may allow for different head and hair types while allowing for adequate skin preparation, liquid or gel application, and signal acquisition.

FIG. 16A illustrates an external view electrode assembly 1600 in a raised position, in accordance with some embodiments. Electrode assembly 1600 comprises upper body portion 1612, lower body portion 1620, and a plurality of elongate elements 1614 connected to the lower body portion. Electrode assembly 1600 also comprises an exterior shell 1610 configured slidably move from a raised position to a lowered position relative to the body portions 1612 and 1620. The electrode assembly may comprise locking means such as a latch to secure the shell relative to the body portions. In the illustrated embodiment, two positions are shown; however, optionally, the position of the shell may be continuously adjustable relative to the body. Additionally, in some embodiments, the exterior shell may comprise a skirt element 1605. The skirt elements may distribute force from a compressible body portion to a wider surface area, which may increase patient comfort. Skirt elements may comprise a flexible material. Optionally, the skirt elements may be removably coupled to the exterior shell of electrode assembly 1600. In some embodiments, the skirt element(s) may be spring-loaded or loaded with a resiliently compressible material relative to the electrode assembly 1600 such that the skirt element(s) may telescope relative to the electrode assembly 1600. The resiliently compressible material may comprise a thermoplastic elastomer, a rubber material, a compressible foam, a compressible open-celled foam, a silicone-based material, to name a few examples.

FIG. 16B and FIG. 16C illustrate electrode assembly 1600 in a lowered position and a raised position, respectively, in accordance with some embodiments. In the illustrated embodiment, the upper body portion may comprise internal stops to limit the range over which the body portions may be raised and lowered. The body portion and the external shell may be secured by a twist-lock or may not comprise a locking feature. Upper body portion 1612 may comprise an entrance aperture 1624, which may be coupled to external dispensers of the present disclosure to allow external filling and/or refilling of the conductive fluid or gel. Optionally, electrode assembly 1600 may comprise a reservoir which may store a conductive fluid or gel. When pressure is applied, for example, from an external dispenser, electrically conductive fluid may flow outward through a channel or aperture formed in the bottom of the electrode assembly. In some embodiments, the elongate elements 1614 comprise apertures 1640 to allow of a conductive fluid; however, apertures may be present elsewhere on a bottom surface of electrode assembly 1600. As additional pressure is applied, the conductive fluid or gel may flow onto patient tissue in contact with a bottom of the electrode assembly. Once the entire flow path is filled with electrically conductive fluid or gel, current may be conducted to a terminal on the electrode assembly, which in turn is connected to a wire or other conductor present in the backing of the electrode carrier system 700.

Figure 17:
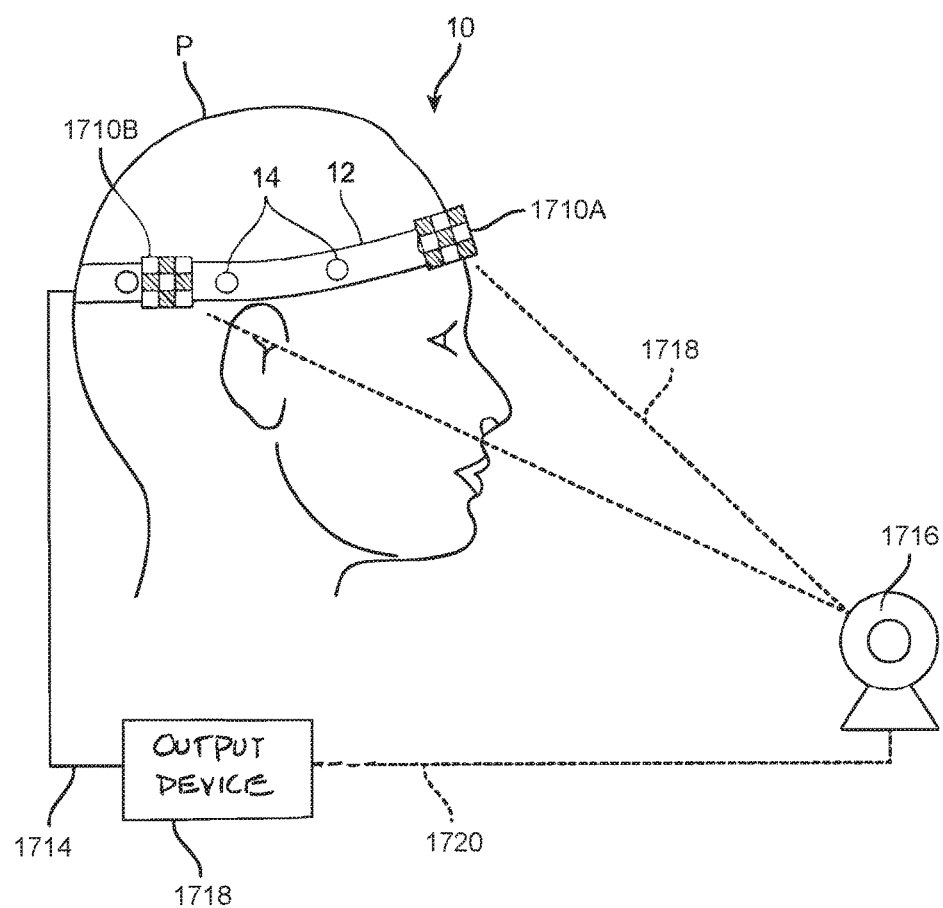
FIG. 17 schematically illustrates an example of optically tracking the movement of a patient in combination with the electrode carrier system.

In further embodiments, the electrode carrier system may be configured as a headband, as illustrated in FIG. 17, and fitted upon a patient P. The electrode carrier system is in electrical communication with a controller and/or output device 1718 via conductive wires 1716. In other variations, the device 1718 may be coupled wirelessly as well. The electrode assemblies 14 may incorporate any of the electrode assembly variations described herein and in any number of combinations, if so desired. In the embodiment illustrated in FIG. 17, the headband backing 12 may further incorporate one or more fiducial markers 1710A, 1710B which allow for the visual tracking of these markers 1710A, 1710B within the field of view of a camera or other optical imager 1716. The markers 1710A, 1710B may include any variety of visual indicators shown in this variation as high-contrast printed patterns having specified shapes, as shown. In other variations, the fiducial markers 1710A, 1710B may include lights such as an arrangement of LEDs.

While two markers are illustrated as an example, additional markers may be further distributed around the circumference of the backing 12 to allow for more precise tracking, e.g., to allow for tracking when the patient's head H may be turned in a manner which obscures one of the markers. As noted, a camera or other optical imager 1716, such as a digital camera, may be positioned in proximity to the patient P during use of the electrode carrier system 10 such that the electrode carrier system 10 and markers 1710A, 1710B remain in the field of view 1718 of the imager 1716. While a single imager 1716 is shown in this example, additional imagers positioned at different locations may also be used in combination to help ensure that the electrode carrier system 10 and markers 1710A, 1710B remain in the field of view 1718 at all times. Additionally, the imager 116 may be optionally motorized with pan and tilt capabilities to ensure that the patient P remains in the field of view 1718 of the imager 1716.

With the electrode carrier system 10 electrically coupled to the controller and/or output device 1718, the imager 1716 may also be connected to the controller and/or output device 1718 by wires or another communications link 1720 or to a second controller and/or output device through wired or wireless communication. In this manner, the controller 1718 may be further programmed with a computer vision algorithm to identify a position and orientation of the patient's head H so that the controller may receive the marker information from imager 1716 to determine patient movement in real time. This information can then be used for artifact rejection and diagnostic purposes. For instance, visual tracking of the markers 1710A, 1710B may be used to determine or confirm whether the patient P is experiencing a convulsive seizure particularly if the patient's detected brain signals are sonified.

Figure 18:
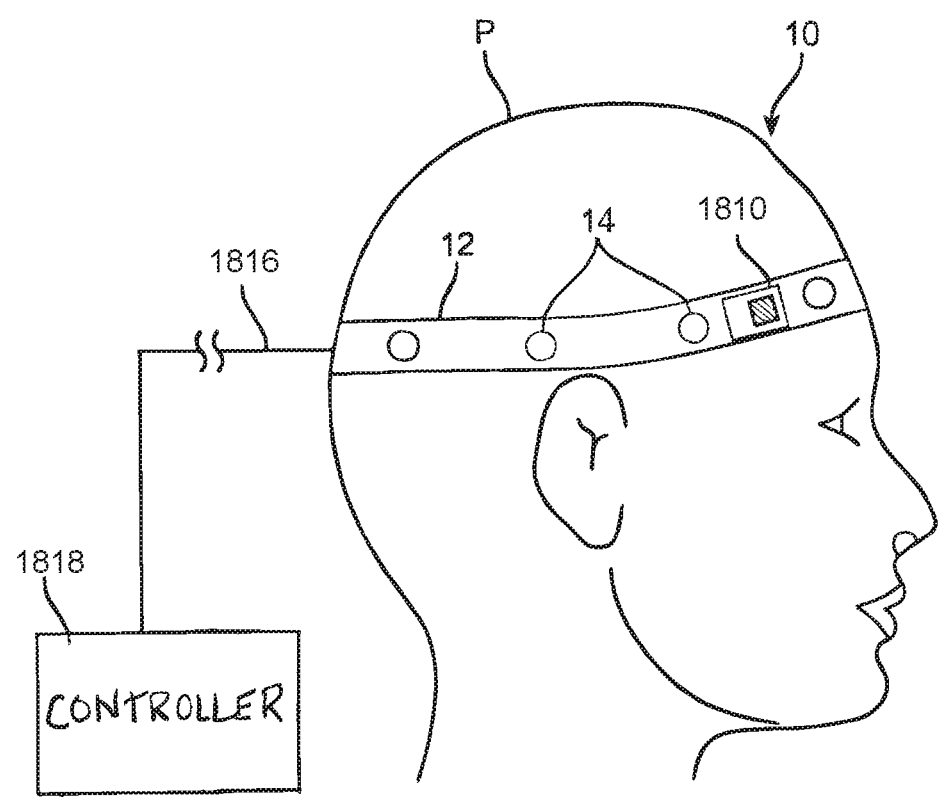
FIG. 18 schematically illustrates another example of utilizing one or more accelerometers for detecting the patient's movements in combination with the electrode carrier system.

In yet another variation, instead of visual markers, the electrode carrier system 10 may incorporate one or more accelerometers 1810 attached within or along the backing 12, as shown in FIG. 18. The one or more accelerometers 1810 may comprise three-axis accelerometer devices which are sensitive enough to detect the movement of the patient's head. This data can be transmitted to the controller and/or output device 1818 via conductive wires 1816 for processing to determine the patient's movements as well as motion artifact rejection. If the detected acceleration exceeds a predetermined threshold, this may be an indicator to the controller that these motion artifacts may be excluded from consideration to prevent the inclusion of artifact noise from other detected data.

The electrode carrier system 10 may be utilized with any combination of electrodes described herein, for example as described with respect to FIGS. 8A-13C, and may also be used in any combination with either the optical motion detection or accelerometer monitoring. In other variations, both the optical motion detection and accelerometer monitoring may be utilized in combination together, if so desired.

The present disclosure provides methods for continuously monitoring a subject using the electrode carrier systems and electrode assemblies described herein. Such methods may comprise placing an electrode carrier assembly comprising one or more electrode assemblies and, optionally, scalp prepares in proximity to a patient skin. A method may comprise accommodating movement of the electrode assembly relative to the electrode carrier system to clear one or more of hair or skin. Optionally, methods of use may accommodate movement of a scalp preparer, which may be a secondary tool or integrated into an electrode assembly. Methods of use may comprise dispensing a conductive fluid or gel onto a patient skin. Dispensing a conductive fluid or gel may, optionally, comprise use of an external dispenser. The conductive fluid or gel may further be at least partially abrasive. Methods of use may comprise collection electrical signals such as for example as part of one or more of an EEG sensor, an EKG sensor, or an EMG sensor. A method may comprise continuously monitoring a subject for a period time which may be 1 second, 10 seconds, 30 seconds, 1 minutes, 10 minutes, 30 minutes, 1 hour, 6 hours, 12 hours, 1 day, 3 days, 1 week, 2 weeks, 1 month, 6 months, 1 year, and, optionally, an period of time defined by a range between any two of the preceding values.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An electrode assembly comprising:
   an electrode body defining an interior reservoir for storing a tissue conductive fluid or gel, the electrode body having an opening to dispense the tissue conductive fluid or gel and a patient contacting surface,
   wherein at least a portion of the electrode body is at least partially adjustable, collapsible, or compressible in a direction toward skin of the patient, in response to a force applied on the electrode body in the direction toward the skin, such that contact area between the patient contacting surface and the patient increases, and
   wherein the at least partially adjustable, collapsible, or compressible portion of the electrode body has a shape tapering toward the opening of the electrode body.

2. The electrode assembly of claim 1, wherein the electrode body comprises a first body member and a second body member operatively coupled to one another.

3. The electrode assembly of claim 2, wherein one or more of the first body member or the second body members are conductive.

4. The electrode assembly of claim 2, wherein the first body member and the second body members are coaxial.

5. The electrode assembly of claim 2, wherein the first and second body members are configured to telescope relative to one another in response to the force applied on the electrode body in the direction toward the skin.

6. The electrode assembly of claim 5, wherein the second body member is spring-loaded within the first body member.

7. The electrode assembly of claim 2, wherein the first body member is rigid and the second body member is flexible and resiliently collapsible in response to the force applied on the electrode body in the direction toward the skin.

8. The electrode assembly of claim 7, wherein the second body member is elastomeric.

9. The electrode assembly of claim 2, wherein the first body member has a cylindrical shape and the second body member is the at least partially adjustable, collapsible, or compressible portion and has a conical shape.

10. The electrode assembly of claim 2, wherein the opening is provided on the second body member.

11. The electrode assembly of claim 10, wherein the electrode body has a central axis and the opening is off-set from the central axis.

12. The electrode assembly of claim 1, wherein the electrode body is at least partially depressible to dispense the tissue conductive fluid or gel through the opening.

13. The electrode assembly of claim 12, wherein the electrode body comprises a depressible top surface or button.

14. The electrode assembly of claim 12, wherein the electrode body comprises a depressible lateral surface or button.

15. The electrode assembly of claim 1, wherein electrode body comprises an adaptor for an external dispenser of the tissue conductive fluid or gel.

16. The electrode assembly of claim 1, wherein the electrode body comprises a skin preparing surface adjacent the opening, and wherein the electrode body is configured to be movable relative to a body of a wearable sensor apparatus to clear one or more of skin or hair of the subject.

17. The electrode assembly of claim 16, wherein the skin preparing surface adjacent the opening of the electrode body is one or more of rigid or abrasive.

18. The electrode assembly of claim 16, wherein the electrode body is movable relative to the body of the wearable sensor by one or more of translation, rotation, or pivoting.

19. The electrode assembly of claim 1, further comprising a protective skirt configured to couple to the electrode body, the protective skirt having an increased surface area base to minimize exposure of skin adjacent the opening of the electrode body to an external environment.

20. The electrode assembly of claim 19, wherein the protective skirt is configured to removably couple to the electrode body.

21. The electrode assembly of claim 19, wherein the protective skirt is spring-loaded onto the electrode body.

22. An electrode assembly configured to be rotatably mounted relative to a carrier system, the electrode assembly comprising:
    an electrode body defining an interior reservoir for storing a tissue conductive fluid or gel, the electrode body having an opening to dispense the tissue conductive fluid or gel and a patient contacting surface,
    wherein the electrode body is at least partially adjustable, collapsible, or compressible in a direction toward skin of the patient, in response to a force applied on the electrode body in the direction toward the skin, such that contact area between the patient contacting surface and the patient increases,
    wherein the electrode body comprises an adapter for an external dispenser of the tissue conductive fluid or gel, the adapter being configured to align a longitudinal axis of the external dispenser with a rotational axis of the electrode assembly.

23. The electrode assembly of claim 22, wherein the adapter is configured to couple to the external dispenser, and the external dispenser comprises one or more of a syringe, a manual squeeze tube, or a roller squeeze tube.

24. The electrode assembly of claim 22, wherein the adaptor is configured to removably couple to the external dispenser such that the external dispenser is movable relative to the electrode body.

25. The electrode assembly of claim 24, wherein the external dispenser comprises a skin preparing surface, and wherein the electrode body is configured to accommodate movement of the external dispenser relative to the electrode body to clear one or more of skin or hair of the subject when the external dispenser is removably coupled to the adaptor and moved.

26. The electrode assembly of claim 25, wherein the skin preparing surface is one or more of rigid or abrasive.

27. The electrode assembly of claim 24, wherein the electrode body is configured to couple to the external dispenser so that the external dispenser is movable relative to the electrode body by one or more of translation, rotation, or pivoting.

28. The electrode assembly of claim 25, wherein the electrode body comprises one or more stencil elements having one or more slots through which the skin preparing surface of the external dispenser are received to guide movement of the external dispenser relative to the electrode body.

29. The electrode assembly of claim 22, wherein the adaptor further comprises a valve to prevent backflow of the tissue conductive fluid or gel.

\* \* \* \* \*